(12) United States Patent
Tornier et al.

(10) Patent No.: US 8,740,981 B2
(45) Date of Patent: Jun. 3, 2014

(54) NUCLEAR IMPLANT

(75) Inventors: Alain Tornier, Saint-Ismier (FR);
Jean-Paul Steib, Strasbourg (FR);
Christian Mazel, Le Plessis Robinson (FR)

(73) Assignee: Clariance, Dainville (FR)

( * ) Notice: Subject to any disclaimer, the term of this patent is extended or adjusted under 35 U.S.C. 154(b) by 602 days.

(21) Appl. No.: 12/419,173

(22) Filed: Apr. 6, 2009

(65) Prior Publication Data

US 2009/0254186 A1   Oct. 8, 2009

Related U.S. Application Data

(60) Provisional application No. 61/042,814, filed on Apr. 7, 2008, provisional application No. 61/042,817, filed on Apr. 7, 2008.

(30) Foreign Application Priority Data

Apr. 4, 2008 (FR) ...................................... 08 01860

(51) Int. Cl.
*A61F 2/44* (2006.01)

(52) U.S. Cl.
USPC ..................... 623/17.16; 623/17.11

(58) Field of Classification Search
USPC ...................... 623/17.11–17.16; 606/254–262
See application file for complete search history.

(56) References Cited

U.S. PATENT DOCUMENTS

| | | | | |
|---|---|---|---|---|
| 3,618,214 A | * | 11/1971 | Armstrong | 433/19 |
| 6,264,695 B1 | * | 7/2001 | Stoy | 623/17.16 |
| 6,746,485 B1 | * | 6/2004 | Zucherman et al. | 623/17.16 |
| 6,818,076 B1 | * | 11/2004 | Farzin-Nia | 148/421 |
| 7,309,357 B2 | * | 12/2007 | Kim | 623/17.13 |
| 7,628,814 B2 | * | 12/2009 | Studer et al. | 623/17.11 |
| 2003/0149483 A1 | * | 8/2003 | Michelson | 623/17.11 |
| 2004/0059418 A1 | * | 3/2004 | McKay et al. | 623/17.16 |
| 2004/0225361 A1 | * | 11/2004 | Glenn et al. | 623/17.12 |
| 2005/0033433 A1 | * | 2/2005 | Michelson | 623/17.11 |
| 2005/0191248 A1 | * | 9/2005 | Hunter et al. | 424/50 |
| 2005/0261684 A1 | * | 11/2005 | Shaolian et al. | 606/61 |
| 2006/0052873 A1 | | 3/2006 | Buck et al. | |

(Continued)

FOREIGN PATENT DOCUMENTS

| | | |
|---|---|---|
| FR | 2717370 A1 * | 9/1995 |
| WO | 00/48532 | 8/2000 |

(Continued)

OTHER PUBLICATIONS

Moreau et al., FR 2 717 370 A1, English language translation of abstract retreived Nov. 21, 2013, 1 page.*

*Primary Examiner* — Ellen C Hammond
*Assistant Examiner* — Jacqueline Johanas
(74) *Attorney, Agent, or Firm* — Young & Thompson

(57) ABSTRACT

The nuclear implant according to this invention constitutes, between two overlying and underlying vertebrae Va, Vb of a spine segment Sr, an intervertebral support device that damps shock and ensures the mobility of the functional unit that is formed by the vertebrae of a vertebral column, whereby the nuclear implant includes a filling element (2) that includes at least one continuous wire (50, 51) that is arranged—inside a nuclear space Es that is obtained after nucleotomy of the intervertebral disk Di—along a profile in the shape of a ring whose stack of coils (55) makes it possible to delimit a central internal space (52).

8 Claims, 36 Drawing Sheets

(56) References Cited

U.S. PATENT DOCUMENTS

| | | | |
|---|---|---|---|
| 2006/0136064 A1* | 6/2006 | Sherman | 623/17.16 |
| 2006/0246105 A1* | 11/2006 | Molz et al. | 424/423 |
| 2007/0005088 A1* | 1/2007 | LeHuec et al. | 606/185 |
| 2007/0055275 A1* | 3/2007 | Schaller | 606/92 |
| 2007/0093906 A1* | 4/2007 | Hudgins et al. | 623/17.16 |
| 2007/0150059 A1* | 6/2007 | Ruberte et al. | 623/17.12 |
| 2008/0195210 A1* | 8/2008 | Milijasevic et al. | 623/17.16 |
| 2009/0012621 A1* | 1/2009 | James et al. | 623/17.16 |
| 2009/0012623 A1* | 1/2009 | Sack et al. | 623/17.16 |
| 2009/0048631 A1* | 2/2009 | Bhatnagar et al. | 606/246 |

FOREIGN PATENT DOCUMENTS

| | | |
|---|---|---|
| WO | 2004/041075 | 5/2004 |
| WO | 2004/082526 | 9/2004 |
| WO | 2006/129027 | 12/2006 |
| WO | 2007/012070 | 1/2007 |

* cited by examiner

US 8,740,981 B2

NUCLEAR IMPLANT

CROSS-REFERENCE TO RELATED APPLICATIONS

This application claims the benefit of U.S. Provisional Application No. 61/042,817, filed Apr. 7, 2008; and French patent application 0801860, filed Apr. 4, 2008, the disclosure of which are incorporated herein in their entirety by reference.

FIELD OF THE INVENTION

This invention relates to a wire nuclear implant that constitutes, between two overlying and underlying vertebrae of a spine segment, an intervertebral support device that damps shock and ensures the mobility of the functional unit that is formed by said vertebrae.

BACKGROUND OF THE INVENTION

The technique of filling by a fine wire is commonly used for treating arterial aneurysms. In this case, the purpose of the filling is to ensure a coagulation of the blood pocket so as to prevent its rupture. This technique has been used in interventional neuroradiology for more than 20 years, under the name of coil technique (platinum coils).

A coil of a strip of viscoelastic material has already been inserted into the disk by Professor Husson. This strip is threaded on up to the nuclear space through the annulus.

The insertion of a wire into the nuclear space can easily be performed percutaneously. The pathways of transpedicular percutaneous access are well known to surgeons and primarily to interventional radiologists, in particular in the implementation of Kyphon balloons in kyphoplasties.

This technique consists in inserting a balloon by transpedicular percutaneous pathway into a fractured vertebra and inflating it to ensure a reconstruction of the vertebra and primarily an intravertebral space into which cement will be injected after the balloon is removed.

The transpedicular access for reaching the discal space in the case of hernias was described for the first time in 1978 by Patterson and Arbit. This technique was then improved with the use of an endoscope that made it possible to obtain the visualization of the internal space of the disk.

According to the patent application WO 2006/129027, a filling element is known that is designed to fill a vertebral body cavity for the creation of a nuclear prosthesis of an intervertebral disk. The filling element is heated in advance to a temperature that is greater than that of the human body to allow its insertion in the form of a flexible strand that forms a snarl that fills the cavity.

SUMMARY OF THE INVENTION

This invention relates to a nuclear implant that constitutes, between two overlying and underlying vertebrae Va, Vb of a spine segment Sr, an intervertebral support device that damps shock and ensures the mobility of the functional unit that is formed by said vertebrae of a vertebral column.

The nuclear implant that constitutes, between two overlying and underlying vertebrae Va, Vb of a spine segment Sr, an intervertebral support device that damps shock and ensures the mobility of the functional unit that is formed by said vertebrae of a vertebral column according to this invention consists of at least one filling element that comprises at least one continuous wire that is arranged, inside a nuclear space Es that is obtained after nucleotomy of the intervertebral disk Di, along a profile in the shape of a ring whose stack of coils makes it possible to delimit a central internal space.

The nuclear implant according to this invention consists of a filling element that comprises, on the one hand, a first wire that forms a first ring inside a nuclear space Es that is obtained after nucleotomy of the intervertebral disk Di, and, on the other hand, a second wire that is arranged to form a ball inside the central internal space that is delimited by the first ring.

The nuclear implant according to this invention consists of a filling element that comprises, on the one hand, a first wire that forms a first ring inside a nuclear space Es that is obtained after nucleotomy of the intervertebral disk Di, and, on the other hand, a second wire that is arranged to form another ring inside the central internal space that is delimited by the first ring.

The nuclear implant according to this invention comprises a central internal space that is delimited by the ring that is obtained by the arrangement of the wire or wires that is filled with a product that can be a gel or a pasty product or a fiber-based product or an injectable viscoelastic material.

The nuclear implant according to this invention comprises a wire that comprises active ingredients that promote the formation of fibroses inside the filling element.

The nuclear plant according to this invention comprises an opaque radio wire that makes it possible to monitor the filling and the arrangement in the form of a ring of the wire inside the nuclear space Es.

The nuclear implant according to this invention comprises a wire that is created from composite materials or braided and bioresorbable materials.

The nuclear implant according to this invention comprises a wire that is arranged along a profile in the shape of a ring and that has a winding axis that is approximately perpendicular to the plates of vertebrae Va, Vb of the spine segment Sr.

The nuclear implant according to this invention comprises a wire that comprises a free end that is narrowed or tapered to prevent injuries to tissue.

The nuclear implant according to this invention comprises a wire that is held in the vertebra Va, Vb by means of a seal or any other means to prevent the migration of said wire.

The nuclear implant according to this invention comprises at least two wire rings that are arranged beside one another in the same nuclear space Es.

This invention relates to an insertion device for the nuclear implant that comprises a threaded cannula or a guide tube with a bent profile, a first or second wire-guide flexible sheath that is inserted inside said threaded cannula or said guide tube with bent profile so that one of the ends of said flexible sheath extends into the inside of the nuclear space Es, while the other end is connected to the means of advance or an instrument that allows the insertion of the wire inside said nuclear space Es.

The insertion device for the nuclear implant according to this invention comprises a threaded cannula that is provided at one of its ends with a threading that ensures its bone anchoring in the corresponding vertebra Vb, with an inner channel that ends by a lateral outlet that is designed to reach the upper plate Ps of the underlying vertebra Vb or lower vertebra Pi of the overlying vertebra Va and a head that comprises on its periphery a reference index that allows the surgeon to visualize the position of the lateral outlet of the inner channel inside the overlying vertebra or underlying vertebra Vb and an extension that ensures the connection of said cannula.

This invention relates to a process for filling a nuclear space Es that is obtained after nucleotomy of the intervertebral disk Di that is provided between two overlying and underlying vertebrae Va, Vb of a spine segment Sr of a vertebral column for the composition of a nuclear implant that consists in inserting—inside the nuclear space Es—a filling element that consists of at least one wire that is arranged in the shape of a ring that comprises a stack of coils that delimits an inside central space.

The process for filling a nuclear space Es according to this invention consists in inserting a second wire that is arranged to constitute a second ring inside the internal central space that is delimited by the wire that is arranged in the shape of a first ring.

The process for filling a nuclear space Es according to this invention consists in inserting a second wire that is arranged to form a ball inside the internal central space that is delimited by the wire that is arranged in the shape of a ring.

The process for filling a nuclear space Es according to this invention consists in inserting a product that is created in the form of a gel or a pasty product or a fiber-based product or an injectable viscoelastic material inside the internal central space that is delimited by the wire that is arranged in the shape of a ring.

The process for filling a nuclear space Es according to this invention consists in that the nuclear implant is inserted by means of an insertion device connected to means of advance or an instrument that allows the insertion of the wire or the product inside said nuclear space Es.

This invention relates to a process for nucleotomy of an intervertebral disk Di by a pathway of transpedicular access at the level of the overlying vertebra Va of a spine segment Sr for the creation of a nuclear space Es, which consists in:
  Positioning and inserting a pin under x-ray monitoring into the pedicle of the overlying vertebra Va of the spine segment Sr,
  Threading a plug onto the pin to reach the pedicle of the overlying vertebra Va of the spine segment Sr,
  Placing on the plug a guide tube that is provided at its end with a threaded portion that allows its anchoring in the pedicle of the overlying vertebra Va,
  Removing the pin and the plug and drilling a hole in the body of the vertebra by means of another guide tube with bent profile that is inserted inside the guide tube so as to create a bone channel Ca in the body of the overlying vertebra Va,
  Inserting in the guide tube with bent profile a flexible cutter that allows the piercing of the lower plate Pi of the overlying vertebra Va,
  Removing the flexible cutter and inserting into the guide tube with bent profile a cutting device that is actuated in rotation so as to allow the nucleotomy of the intervertebral disk Di by cutting, in a controlled manner, the maximum "nucleus pulposus" (NP) of the intervertebral disk Di to make possible the creation of the nuclear space Es,
  Aspirating the debris by means of an injection and suction system that is introduced into the nuclear space Es through the guide tube with bent profile.

This invention relates to a process for nucleotomy of an intervertebral disk Di by a pathway of transpedicular access or at the level of the overlying vertebra Va or at the level of the underlying vertebra Vb of a spine segment Sr for the creation of a nuclear space Es that consists in:
  Positioning and inserting a pin under x-ray monitoring into the pedicle of the overlying vertebra Va or the underlying vertebra Vb of the spine segment Sr,
  Threading a plug onto the pin to reach the pedicle of the overlying vertebra Va or the underlying vertebra Vb of the spine segment Sr,
  Placing on the plug a guide tube that is provided at its end with either points or a threaded portion that allows an anchoring in the pedicle of the overlying vertebra Va or underlying vertebra Vb,
  Removing the pin and the plug and drilling a hole in the body of the vertebra by means of a cannula bit that is inserted inside the guide tube so as to create a bone channel Ca in the pedicle of the overlying vertebra Va or the underlying vertebra Vb,
  Removing the cannula bit and the pin to insert into the bone channel Ca a cannula that is provided at one of its ends with a threading that ensures its bone anchoring,
  Positioning the lateral orifice of the threaded cannula in the direction either of the lower plate Pi of the overlying vertebra Va or of the upper plate Ps of the underlying vertebra Vb to be able to reach the upper or lower surface of the intervertebral disk Di,
  Perforating either the lower plate Pi of the overlying vertebra Va or the upper plate Ps of the underlying vertebra Vb and the lower surface of the intervertebral disk Di by means of a bit or a flexible square point that is inserted inside the bore of the threaded cannula to reach the internal structure that is designated "nucleus pulposus" (NP) of said intervertebral disk Di,
  Initiating the nucleotomy of the intervertebral disk Di by eliminating, in a controlled manner, the maximum "nucleus pulposus" (NP) of the intervertebral disk Di through the threaded cannula,
  Inserting—by means of the threaded cannula and into the intervertebral disk Di—an extraction device with a small diameter that comprises, for example, a laser fiber, an optical fiber that is connected to a camera, an irrigation hole, and an aspiration hole,
  Removing the "nucleus pulposus" (NP) so as to release a nuclear space Es.

This invention relates to a method for replacing a nucleus pulposus of an intervertebral disk after a nucleectomy, the intervertebral disk being located between an ending plate of a lower vertebra and an ending plate of an upper vertebra, the intervertebral disk having an annulus encircling a vertical axis, the annulus having a peripheral inner wall, and wherein after the nucleectomy the peripheral inner wall and the ending plates define a nucleus space, and one of the ending plates has a boring channel extending therethrough, the boring channel having a distal end with an opening located adjacent to the vertical axis, said method comprising insertion through the boring channel and into the nucleus space of a wire such as to form an implant, the wire having a distal portion and being made of a radio-opaque material, said insertion being made such that:
  the distal portion of the wire abuts against the ending plate opposite to the boring channel; then said insertion being made such that
  the wire curves relative to the vertical axis, and defines a stacked outer helix encircling the vertical axis, wherein the stacked outer helix has an outer surface and an inner surface, wherein the outer surface is concentrically located adjacent to the peripheral inner wall and wherein the stacked outer helix is in contact with both ending plates; and then said insertion being made such that
  the wire further curves relative to the vertical axis, and defines a plurality of stacked inner helices each encircling the vertical axis, each of the plurality of stacked inner helices having an outer surface and an inner surface, wherein the outer surface of one of the plurality of stacked inner helices is concentrically located adjacent to the inner surface of the outer helix and wherein the stacked inner helices are in contact with both ending plates;

wherein said insertion is ended when the wire (i) substantially fills the nucleic space, or (ii) partially fills the nucleic space such that one of the plurality of stacked inner helices define a central space.

Preferably, the stacked outer helix is a first stacked outer helix, the plurality of stacked inner helices is a first plurality of stacked inner helices, the central space is a first central space, and the second wire being made of a radio-opaque material and having a distal portion, said insertion of the second wire being made such that:

the distal portion of the second wire abuts against the ending plate opposite to the boring channel; then said insertion being made such that the second wire curves relative to the vertical axis, and defines a second stacked outer helix encircling the vertical axis, wherein the second stacked outer helix has an outer surface and an inner surface, wherein the outer surface of the second outer helix is concentrically located adjacent to the inner surface of the one of the first plurality of stacked inner helices defining the central space, and wherein the second stacked outer helix is in contact with both ending plates; and then said insertion being made such that the second wire further curves relative to the vertical axis, and defines a second plurality of stacked inner helices each encircling the vertical axis, each of the second plurality of stacked inner helices having an outer surface and an inner surface, wherein the outer surface of one of the second plurality of stacked inner helices is concentrically located adjacent to the inner surface of the second outer helix, and wherein the second stacked inner helices are in contact with both ending plates;

wherein said insertion is ended when the second wire (i) substantially fills the first nucleic space, or (ii) partially fills the first nucleic space such that one of the second plurality of stacked inner helices define a second central space.

BRIEF DESCRIPTION OF THE DRAWINGS

The accompanying drawings, provided by way of example, will make it possible to better understand the invention, the characteristics that it exhibits, and the advantages that it is able to ensure.

DETAILED DESCRIPTION OF THE INVENTION

Figure 1:
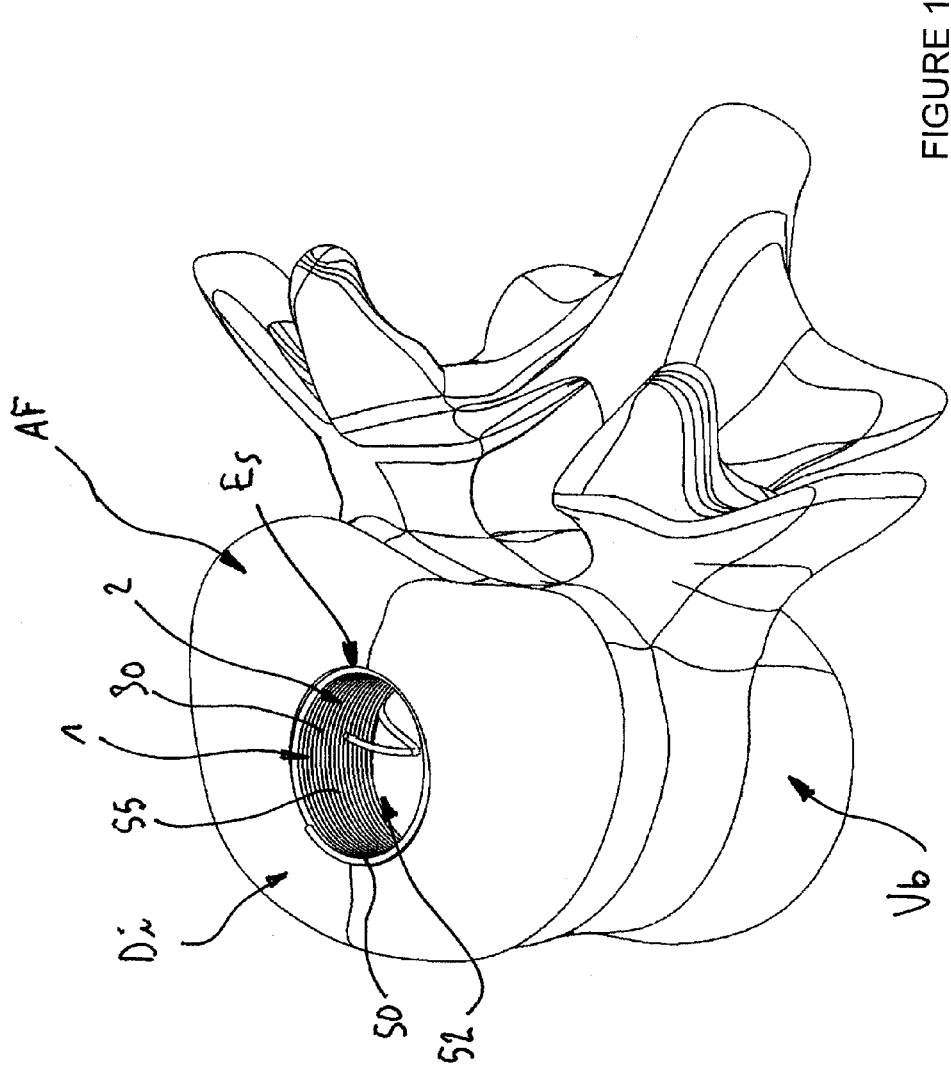
FIG. 1 is an exploded perspective view that illustrates the nuclear implant according to this invention whose filling element consists of a wire that is arranged in a ring.

Various embodiments of arrangement and composition of a nuclear implant 1 according to this invention are illustrated in FIGS. 1, 2, 18 and 34 to 36. To be verified:

The nuclear implant 1 consists of at least one filling element 2 that comprises at least one continuous wire 50 that is arranged in the form of a ring and whose stack of coils 55 makes it possible to delimit a central internal space 52 when said coils are wound on the inside of a nuclear space Es that was previously provided in the intervertebral disk Di of two overlying and underlying vertebrae Va, Vb of a spine segment Sr.

The nuclear implant 1 consists of a wire 50 whose quasi-contiguous winding of coils 55 in ring form delimits a central internal space 52 and a certain number of gaps 30 between each coil.

The ring of coils 55 is formed by several contiguous wire layers 50 whose winding axis is approximately perpendicular to the plates of vertebrae Va, Vb of the spine segment.

Figure 2:
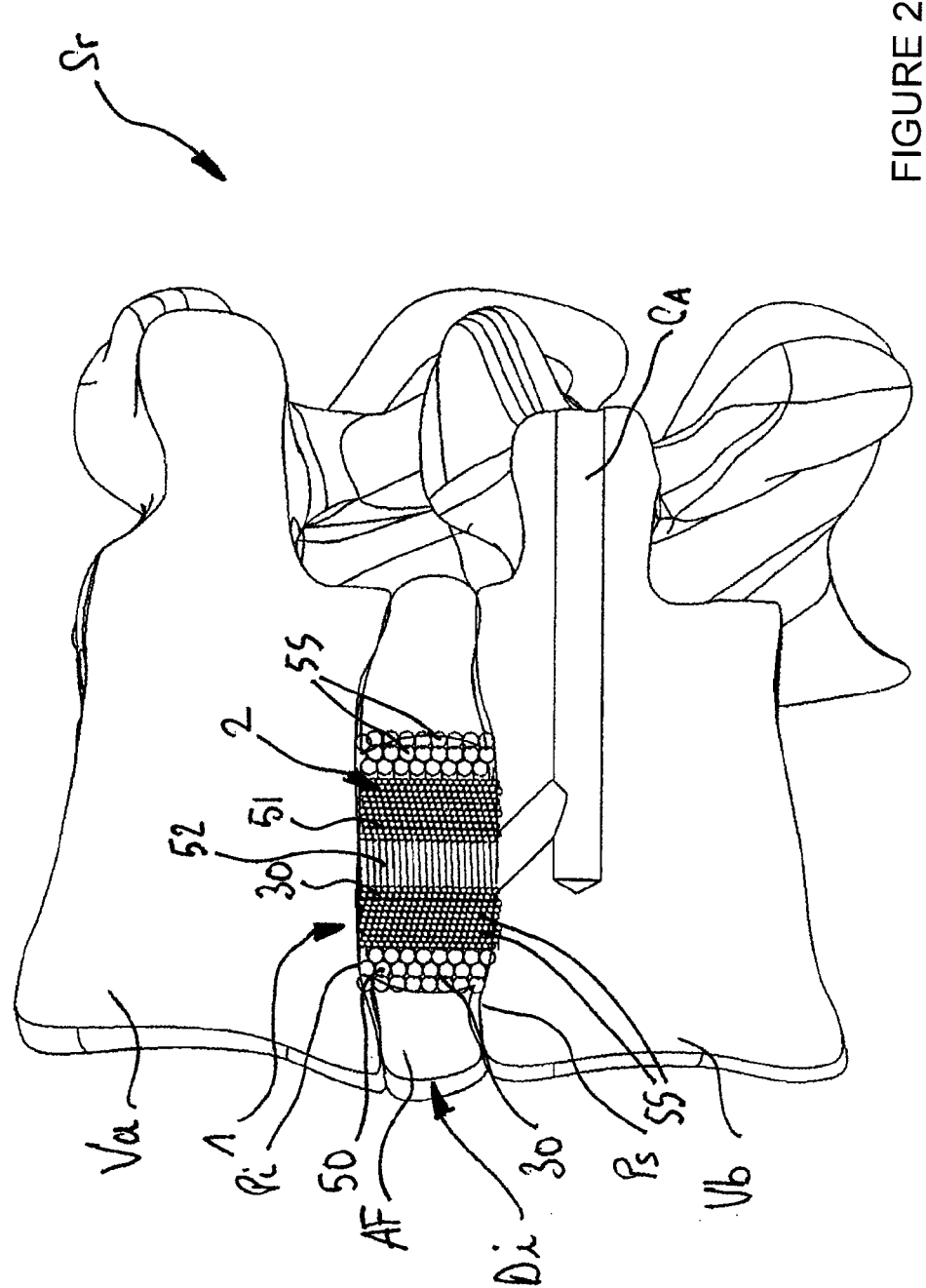
FIG. 2 is a cutaway view that illustrates the nuclear implant according to this invention whose filling element consists of two wires that are arranged in a ring.
Figure 36:
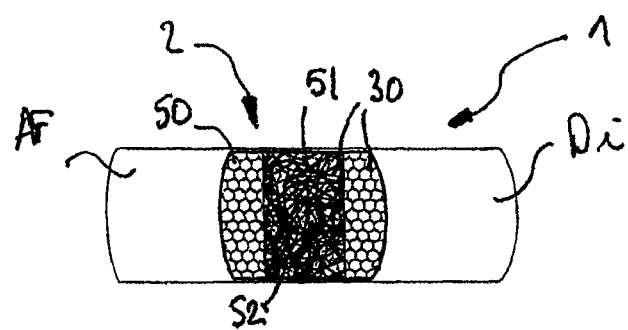

A second wire 51 can be placed inside the central internal space 52 that is delimited by the winding of the wire 50, and said second wire can be arranged either according to a second ring or according to a ball, or according to both and delimiting other gaps 30, making it possible to create the filling element 2 (FIGS. 1, 2, 36).

The wire or wires 50, 51 are provided in biocompatible form, with a small diameter or with different diameters based on the composition of the nuclear implant 1. Regarding the creation of a nuclear implant 1 by means of a single wire 50 that is arranged in a ring, the latter has an outside diameter that is encompassed, for example, between 0.4 and 0.8 millimeter.

The wire or wires 50, 51 can be inert or comprise active ingredients that have as their object to promote the development of fibrotic tissue inside the nuclear space Es that was previously provided in the intervertebral disk Di of two overlying and underlying vertebrae Va, Vb of a spine segment Sr.

The wire or wires 50, 51 are created from bio-resorbable composite materials that may or may not be braided and that may or may not contain active ingredients that are designed to promote the composition of a fibrosis, thus creating a "neo-nucleus."

The wire or wires 50, 51 are radio-opaque, which makes it possible to monitor their insertion into the nuclear space Es prior to the procedure and the post-operative tracking of the nuclear implant 1.

The wire or wires 50, 51 comprise a free end, i.e., the one that penetrates inside the nuclear space Es, which is narrowed or tapered and curved to avoid injuries to the tissue because of its weak resistance to contact, in particular during its insertion into the nuclear space Es.

According to its arrangement in the shape of a ring, the nuclear implant 1 comprises a large number of gaps 30 of different dimensions that are obtained by the stack of coils 55 and that promote the formation of a fibrosis inside the nuclear space Es.

Figure 18:
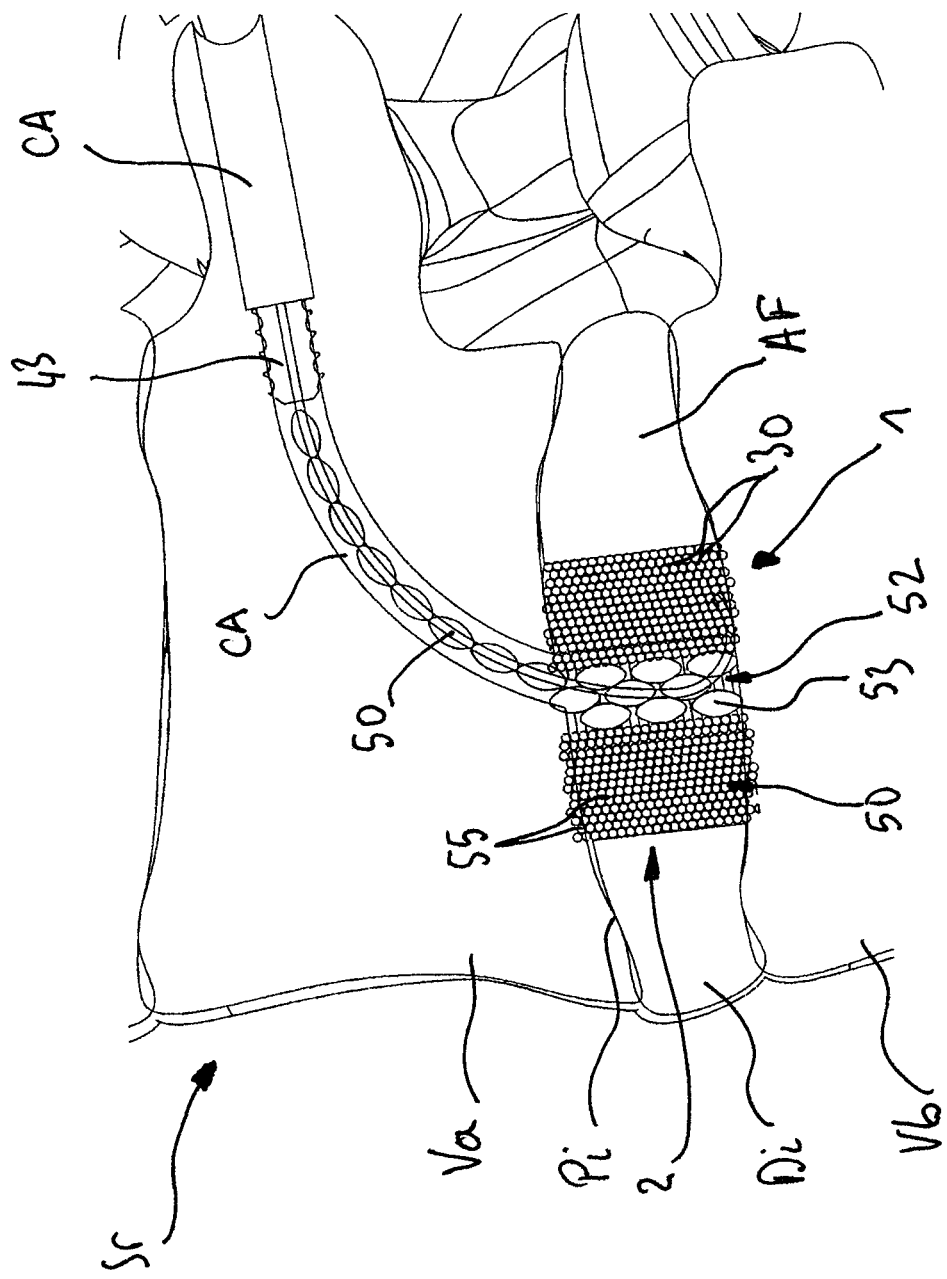
FIG. 18 is a view that shows the insertion of a product that is created in the form of a gel or a pasty product or a fiber-based product or an injectable viscoelastic material inside the central internal space that is formed by the ring of the first wire of the nuclear implant by a pathway of transpedicular access at the level of the overlying vertebra Va according to this invention.
Figure 35:
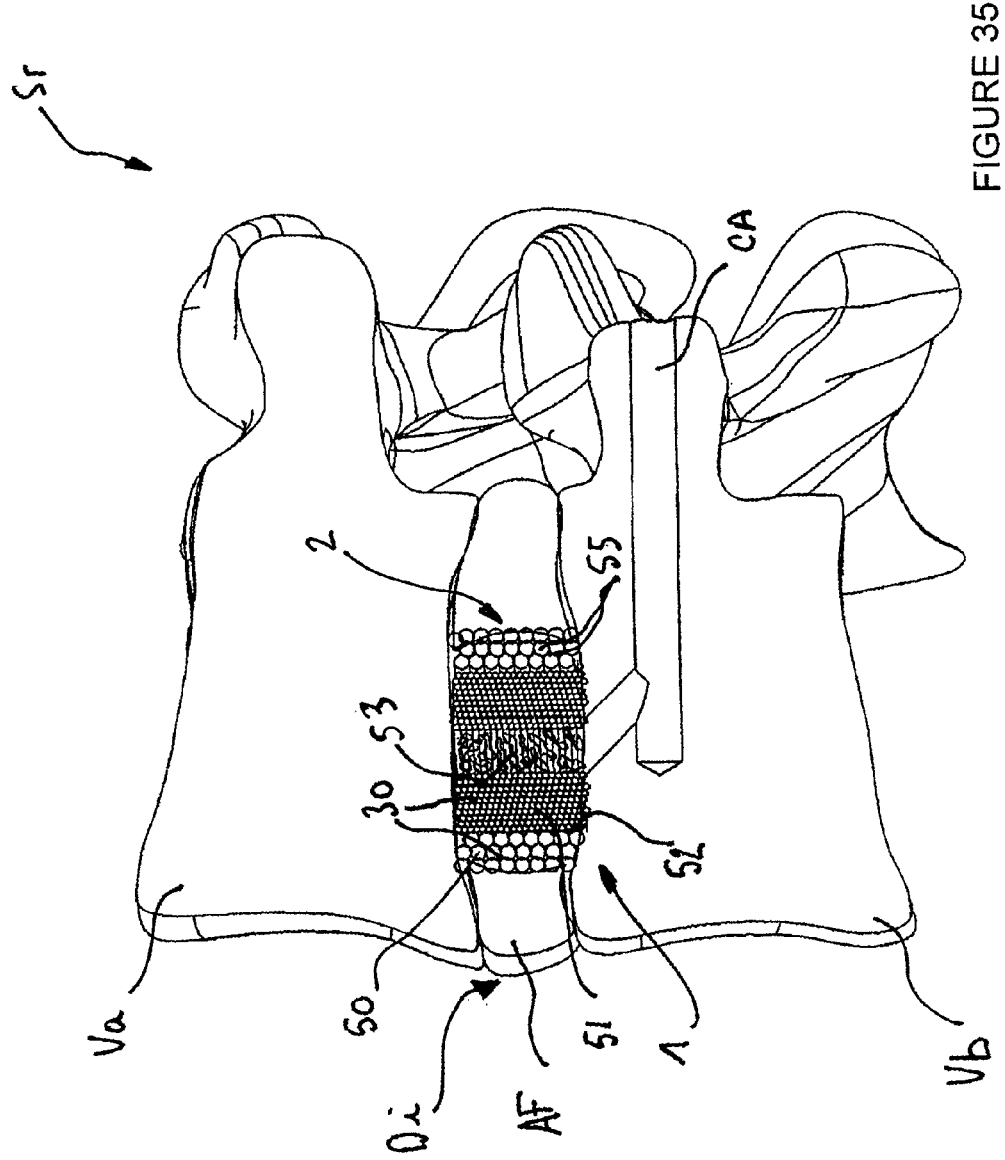

The nuclear implant 1 can comprise, inside the central internal space 52 created from the wire 50 or the arrangement of wires 50, 51, a product 53 that can be a gel or a pasty product or a fiber-based product or an injectable viscoelastic material in viscous or liquid form so as to constitute a pseudo-nucleus (FIGS. 18, 35).

The thus obtained filling element 2 forms a "neo-nucleus"-type nuclear implant 1 that has good mechanical characteristics of cohesion and shock absorption when it consists of, for example, a first wire ring 50 that forms a related "pseudo-annulus" either with a second ring or wire ball 51, or with a product 53 that can be a gel or a pasty product or a fiber-based product or an injectable viscoelastic material that forms a "pseudo-nucleus."

When compression is exerted on the filling element 2, it has been observed that said filling element entrains forces of contact on the wires 50, 51, locking them to one another. This locking provides to the nuclear implant 1 a consistency that allows good mechanical behavior with compression forces and stability of the structure. The denser this structure is, the more rigid the behavior of the filling element 2.

This filling element 2 makes it possible to ensure good resistance to the required compression for a nuclear implant 1 while limiting the lateral forces. The limitation of the lateral forces in particular on the "annulus fibrosus" (AF) is a key point for such an implant so as to prevent the nervous compression phenomena that can take place by the external bulge of the "annulus fibrosus" (AF) of the intervertebral disk Di or by a discal hernia.

Thus, the nuclear implant 1 according to this invention forms a substantial mass filling the discal space that is created after nucleotomy.

The wire or wires 50, 51 have a sufficient rigidity to be able to form a ring that consists of the stack of almost-contiguous coils 55 that are coiled up, by a buckling effect, inside the nuclear space Es.

The thus constituted nuclear implant 1 according to this invention forms a substantial mass that fills the discal space Es that is obtained after nucleotomy.

The nuclear implant 1 according to this invention can comprise at least two wire rings 50 that are arranged beside one another in the same nuclear space Es. In a special case, two transpedicular accesses are created at the level of each pedicle of the same vertebra.

Nucleotomy of the Intervertebral Disk

FIGS. 3 to 12 and 19 to 29 show two overlying and underlying vertebrae Va, Vb of a spine segment Sr of a vertebral column whose intervertebral disk Di will undergo a nucleotomy by a pathway of transpedicular access.

This nucleotomy of the intervertebral disk Di will allow the insertion of a nuclear implant 1 whose ring-shaped structure comprises a central internal space 52 that is delimited by the winding of coils 55.

For this purpose, the intervertebral disk Di comprises an internal structure that is designated "nucleus pulposus" (NP) that is surrounded by a fibrous ring that is referred to as "annulus fibrosus" (AF).

The biochemical composition of the "nucleus pulposus" (NP) consists for the most part of a hydrogel in which the dominant molecules consist of glycosaminoglycans, within which particular cells with "nucleus pulposus" (NP) are suspended. The in-situ biological environment is rather acidic and anaerobic, which can hamper the cellular growth.

The glycosaminoglycans are biological polymers that consist of long glycosidic chains (the constituent monomer is a member of the family of sugars), comprising amino or peptide derivatives, hence their other name of proteoglycan. These polymers are in general very hydrophilic.

The glycans constitute the matrix in which the cells are maintained. The matrix is in very close contact with the osteochondral zone of the lower and upper vertebral plates (cranial and caudal) of the overlying and underlying vertebrae Va, Vb. This zone is the only one that allows rare nutrient exchanges with the "nucleus pulposus" (NP).

The cells that are present in the "nucleus pulposus" (NP), although in a very small quantity, are obtained from embryonic cells, namely "chondrocytic"-type cells and larger, vacuolated cells that are obtained from notochordal lines.

The latter quickly decrease with age; even their metabolism is affected by the acidic conditions that appear with mechanical stress and reduce their potential to regenerate the matrix.

Thus, the mechanical stress that is due to millions of cycles of stresses on the "nucleus pulposus" (NP) generates acidic conditions (lactate) that would prevent the cells from renewing the matrix stock.

The penetration by a plate of overlying or underlying vertebrae Va, Vb of the spine segment Sr in the "nucleus pulposus" (NP) of the intervertebral disk Di makes it possible to carry out the nucleotomy of the latter while allowing the diffusion of blood cells in the nuclear space Es promoting the conditions of a formation of a fibrosis.

Insertion of the Nuclear Implant 1 into a Wire 50 by a Pathway of Transpedicular Access at the Level of the Overlying Vertebra Va of a Spine Segment Sr (FIGS. 3 to 17)

The transpedicular pathway offers the following advantages relative to the standard annular pathway:

Prevents the degradation of the annulus by the instruments of nucleotomy,

Provides a quasi-central and vertical access relative to the plate of the vertebra and in the nuclear space Es, which is essential for allowing the insertion of a wire 50, 51 to constitute an intervertebral stay in the shape of a ring with a vertical axis, Provides the possibility of closing the nuclear space Es by the closing of the transpedicular bone channel Ca by means of a seal or any other means.

Figure 3:
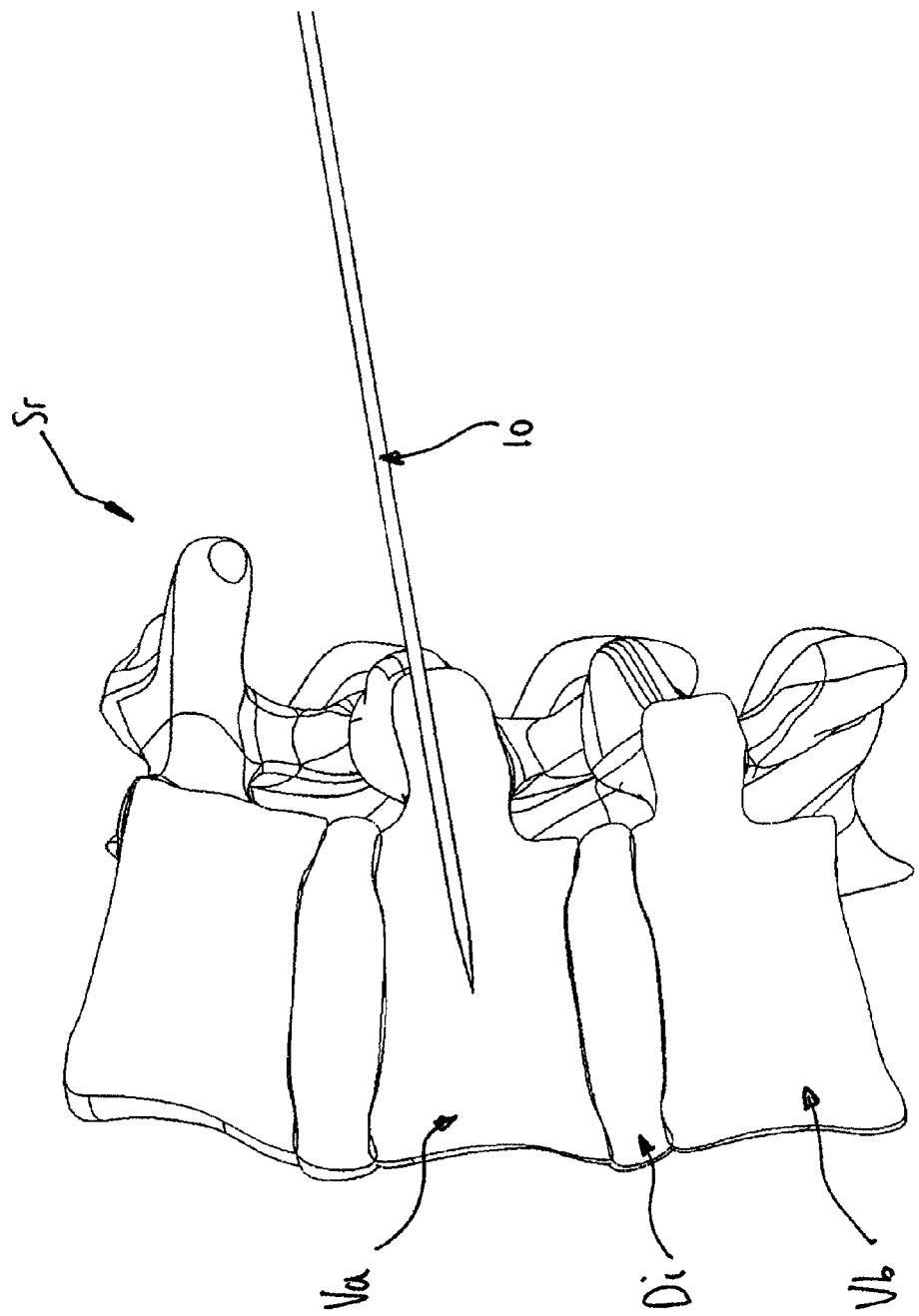
FIGS. 3 to 17 are views that show an embodiment of the various stages that allow the insertion of the nuclear implant by a pathway of transpedicular access at the level of the overlying vertebra Va of a spine segment Sr according to this invention.

Thus, the pedicular view, the nucleotomy of the intervertebral disk Di and the insertion of the nuclear implant 1 are conducted in the following manner by the surgeon:

The surgeon positions and inserts a guide pin 10 under x-ray monitoring into the pedicle of the overlying vertebra Va of the spine segment Sr (FIG. 3). The insertion of the guide pin 10 is carried out from an entry point that is provided at the level of one of the two pedicles of the overlying vertebra Va and by aiming the point of the vertebral body that cuts the vertical line that passes through the center of the nucleus (NP).

Figure 4:
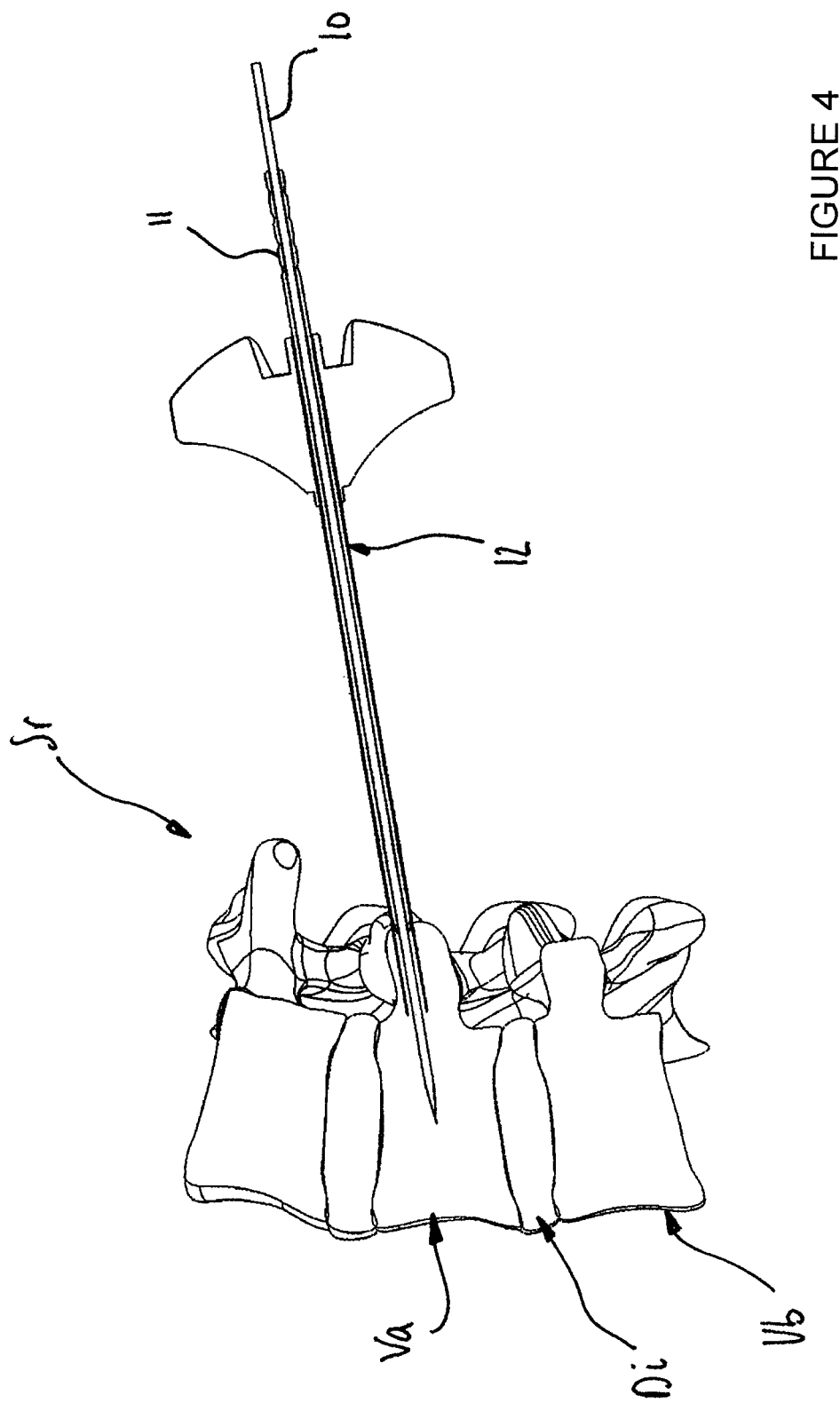

The surgeon threads a plug 11 onto the guide pin 10 to reach the pedicle (FIG. 4).

Figure 5:
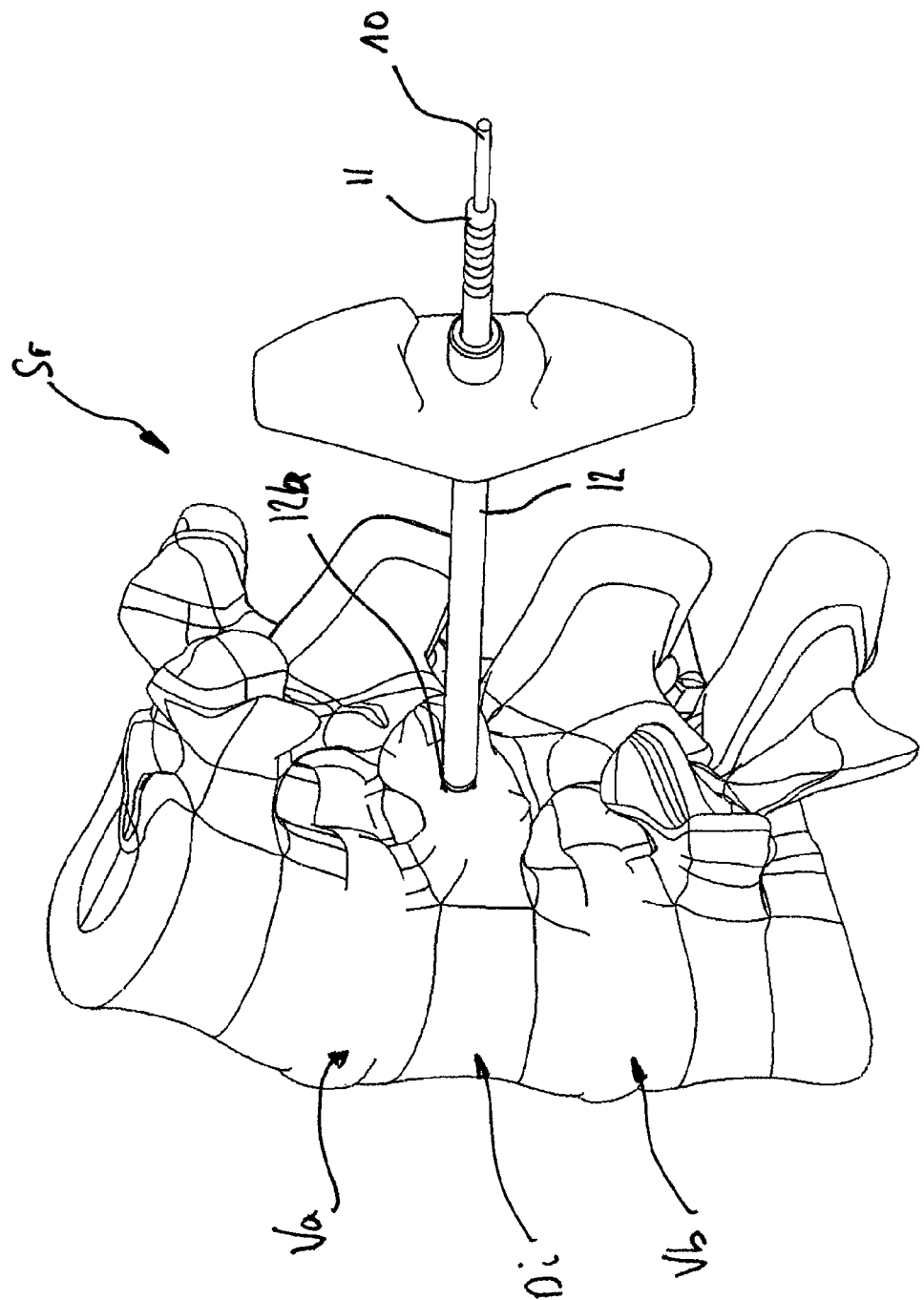

On the plug 11, the surgeon positions a guide tube or straight cannula 12 that is provided at its end with a threaded portion 12b that makes possible a solid anchoring in the body of the overlying vertebra Va (FIGS. 4 and 5). Thus, the guide pin 10 defines the path of the straight cannula 12 that is inserted by screwing to a point beyond the posterior wall of the vertebral body so as to create a bone channel for transpedicular guiding Ca and to protect the neurological elements against any potential damage. The axis of the straight cannula 12 passes vertically from the center of the nucleus (NP) that is located below. The axis of the straight cannula 12 in the sagittal plane, the position of its end in the vertebra, and the dimensions of the vertebra Va itself determine the profile of a curved guide tube or a curved cannula 13a that is adapted to the case.

Figure 6:
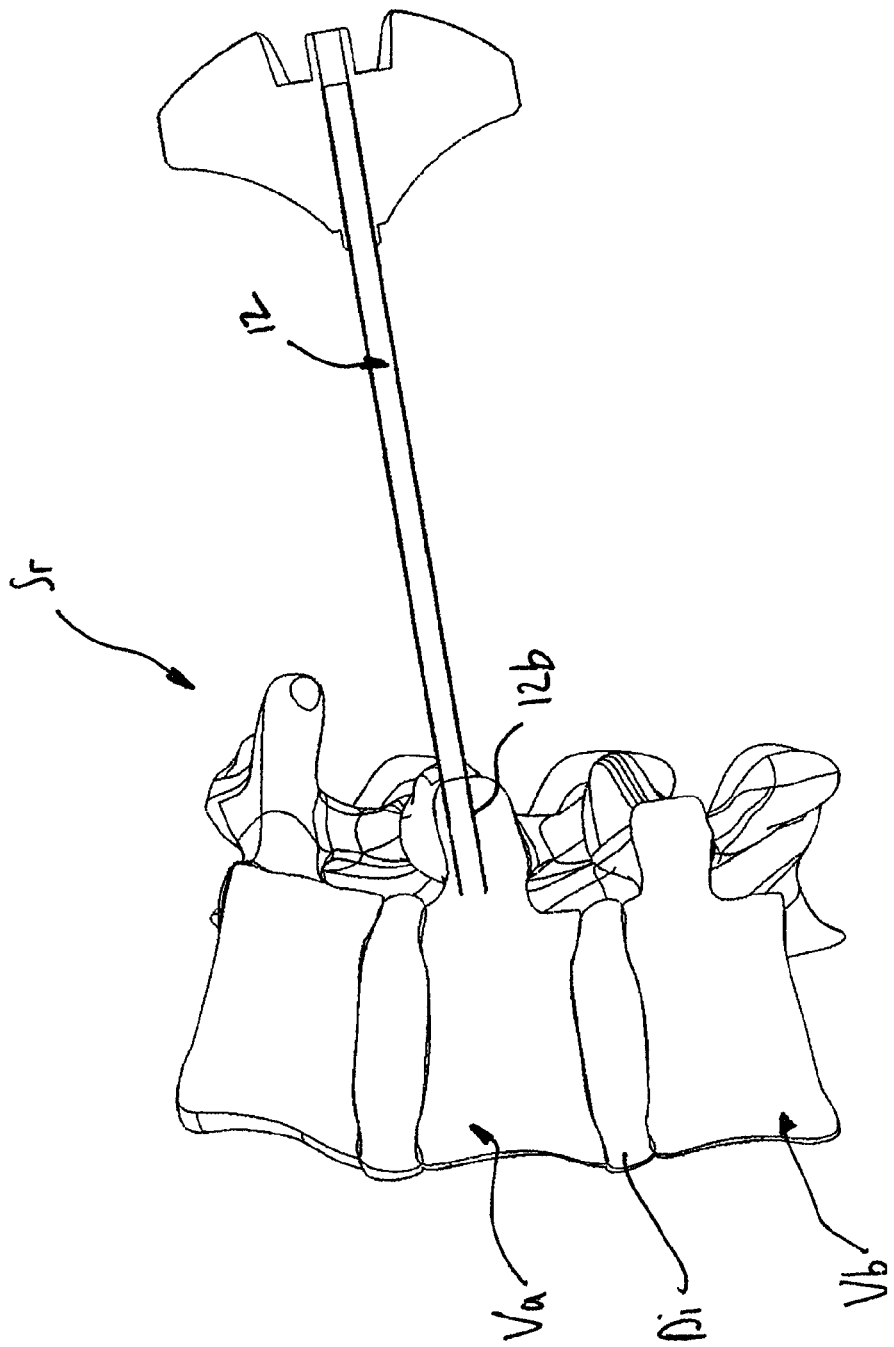
Figure 7:
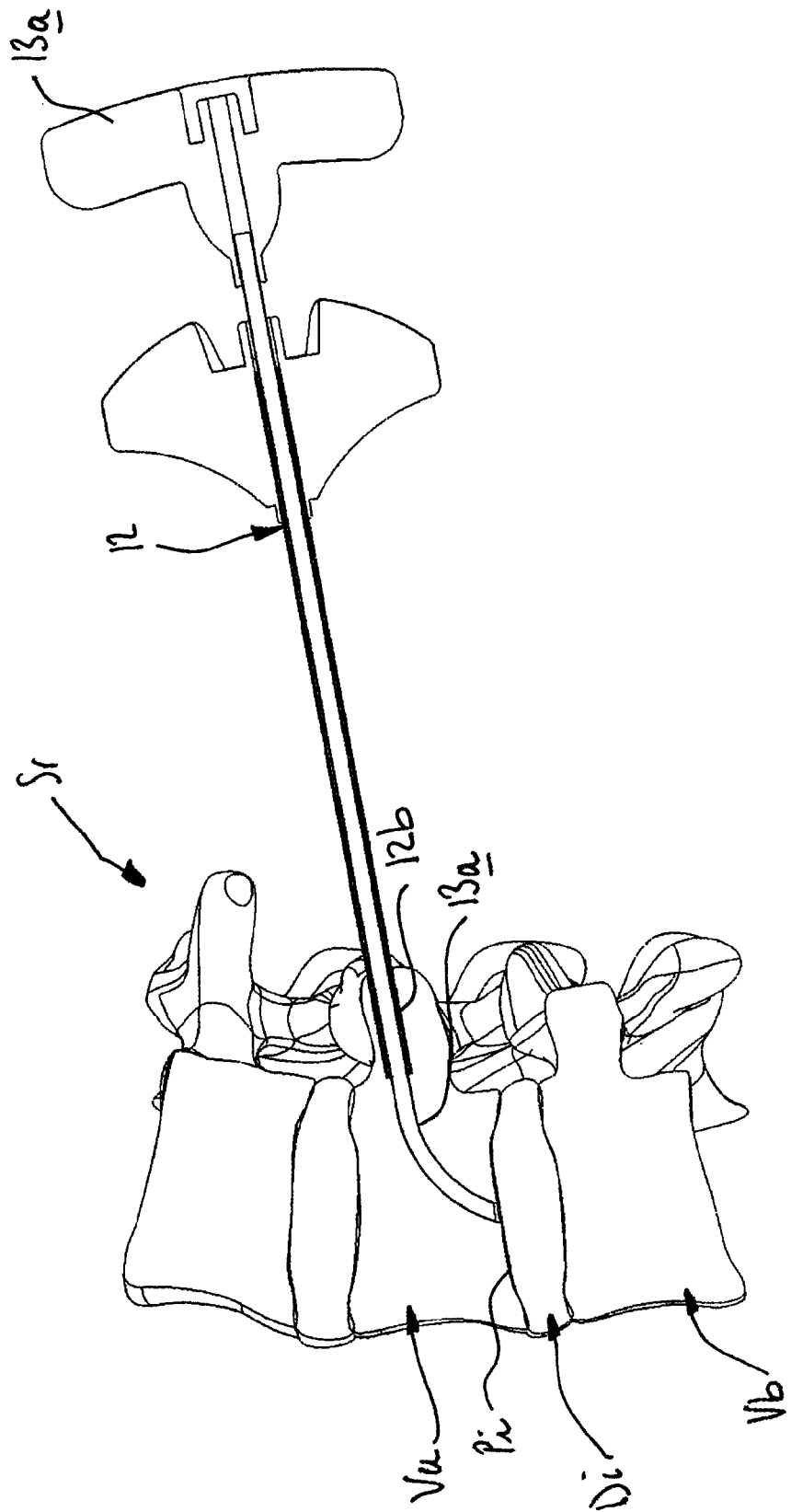

The surgeon removes the pin 10 and the plug 11 and inserts—into the guide tube or straight cannula 12—a second curved guide tube or curved cannula 13a that makes it possible to provide a bone channel for transpedicular guiding Ca up to the level of the lower plate Pi of the overlying vertebra Va (FIGS. 6, 7). The curved cannula 13a is created from super-elastic material and gradually pushed through the straight cannula 12 to exit from the latter by curving until it reaches the lower plate Pi of the vertebra Va. The guiding that is obtained by the straight cannula 12 and the selection of the profile of the curved cannula 13a make it possible easily to reach the point on the plate Pi that is selected during the planning prior to the procedure.

Figure 8:
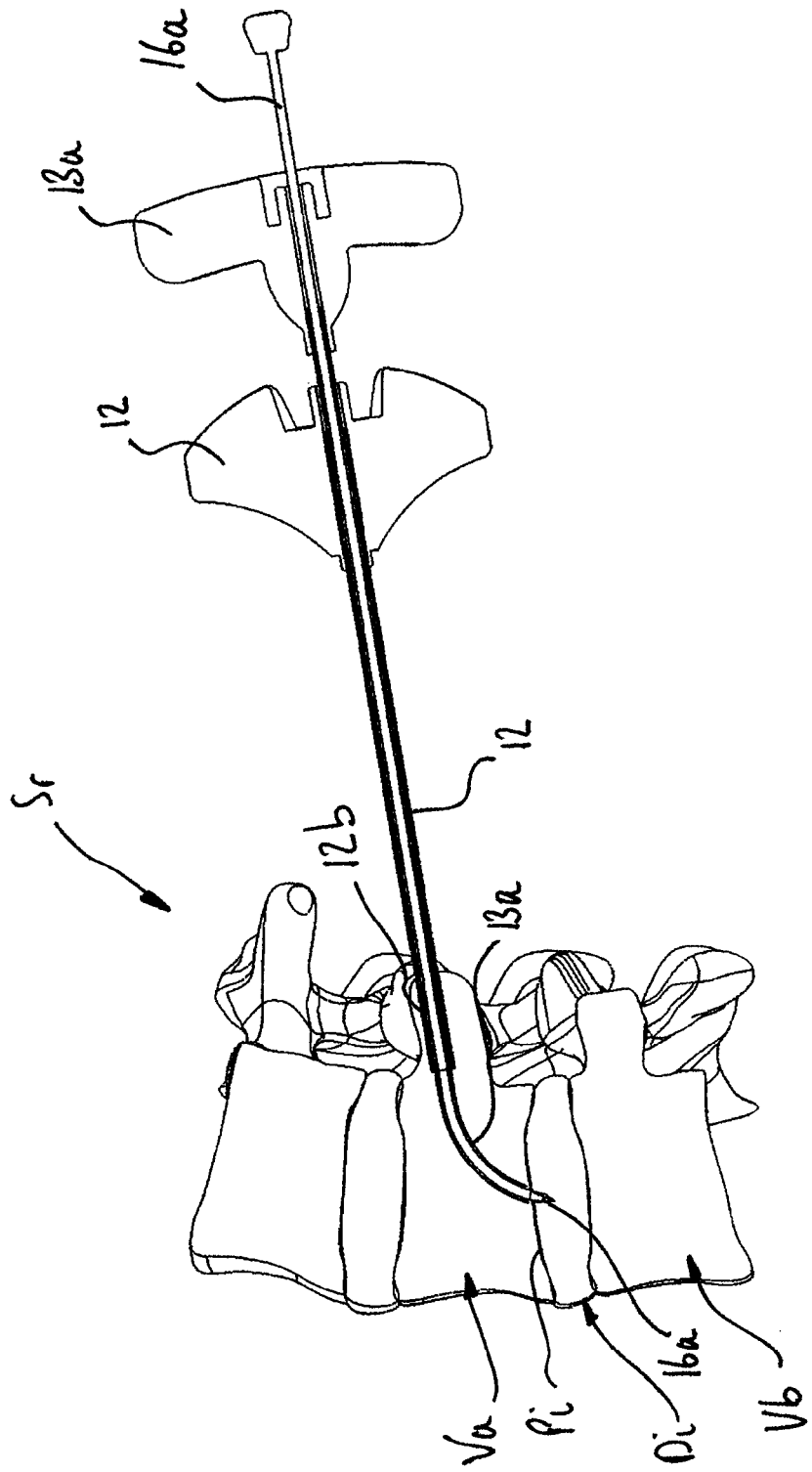
Figure 9:
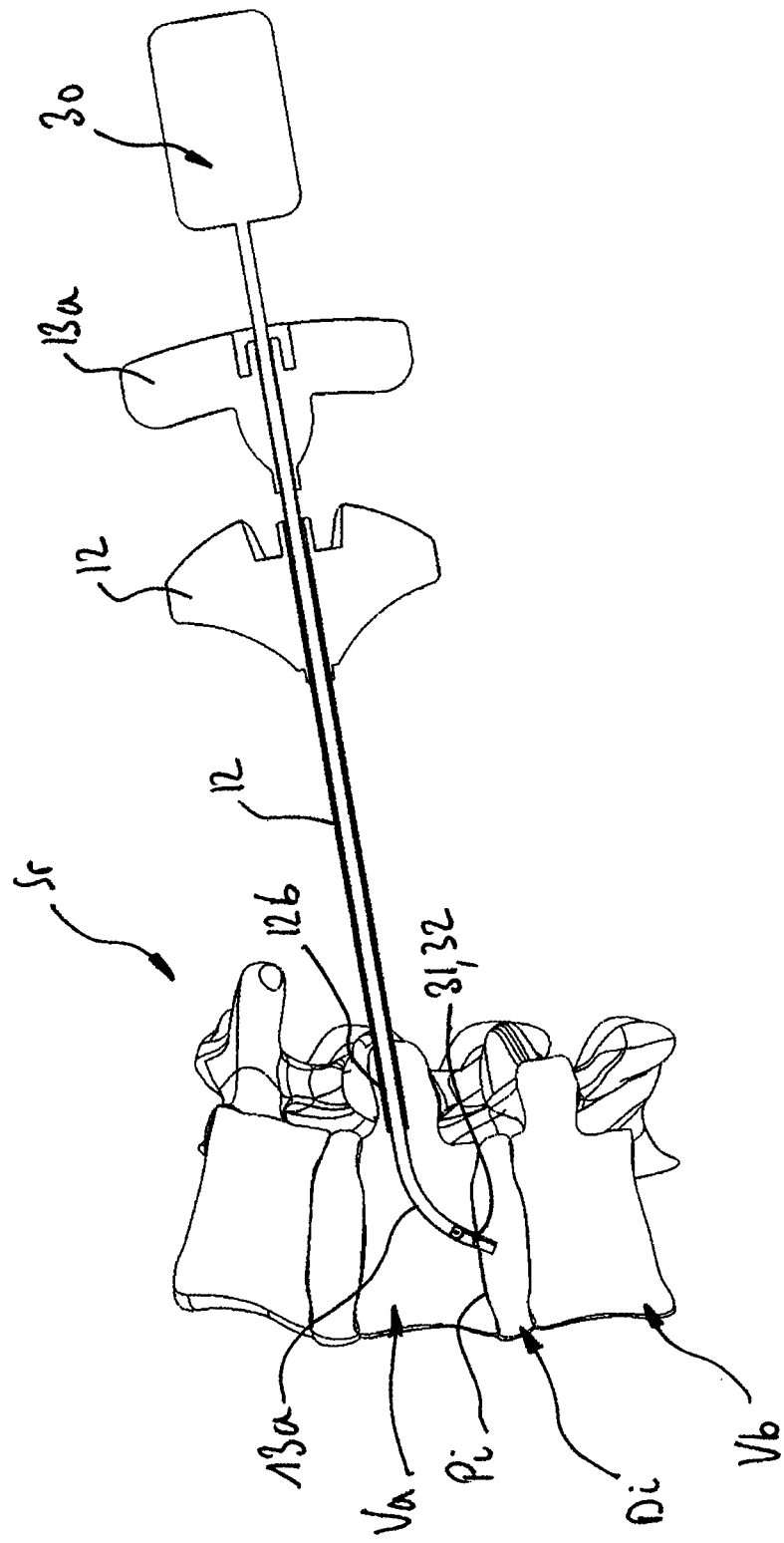
Figure 10:
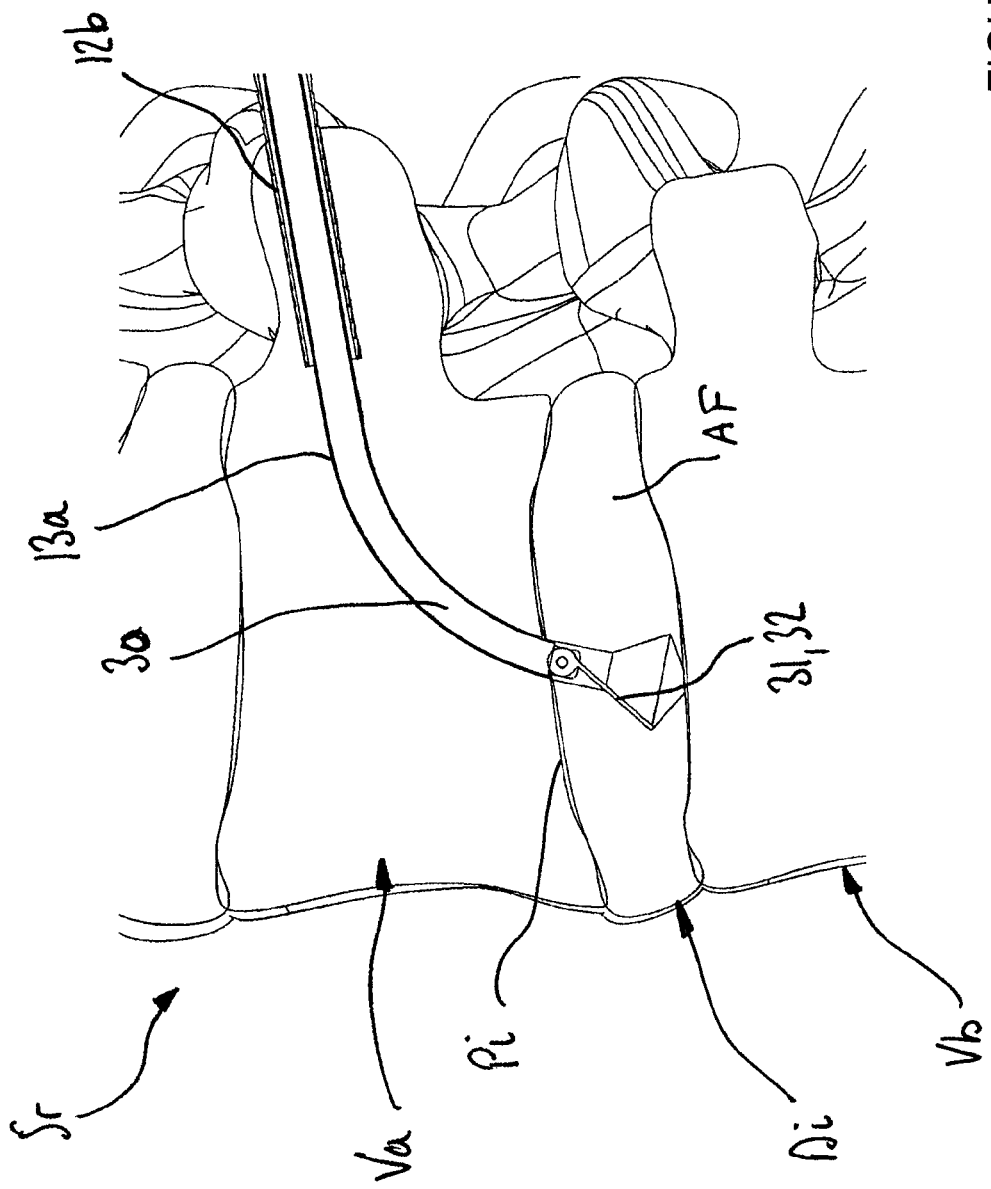
Figure 11:
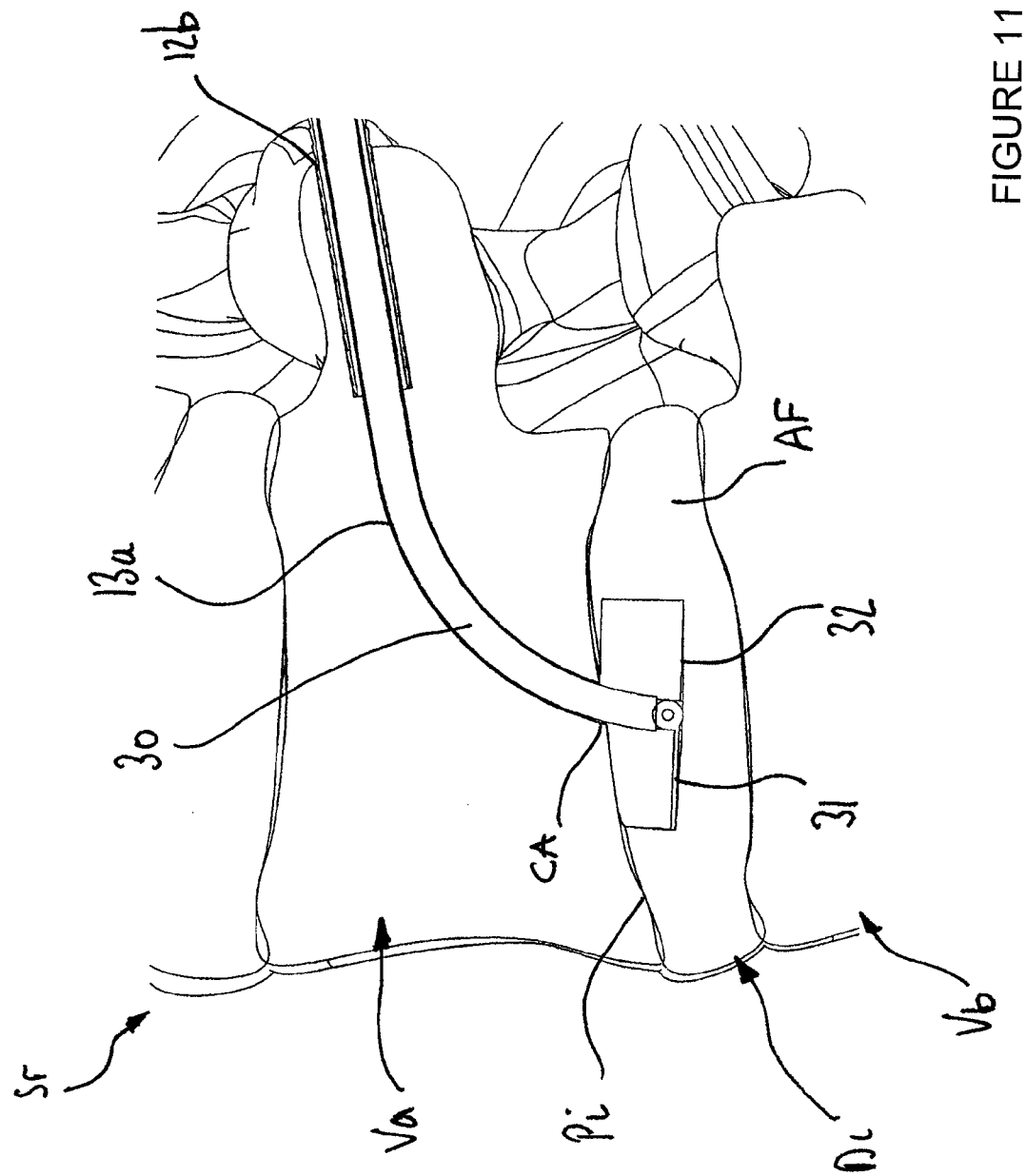
Figure 12:
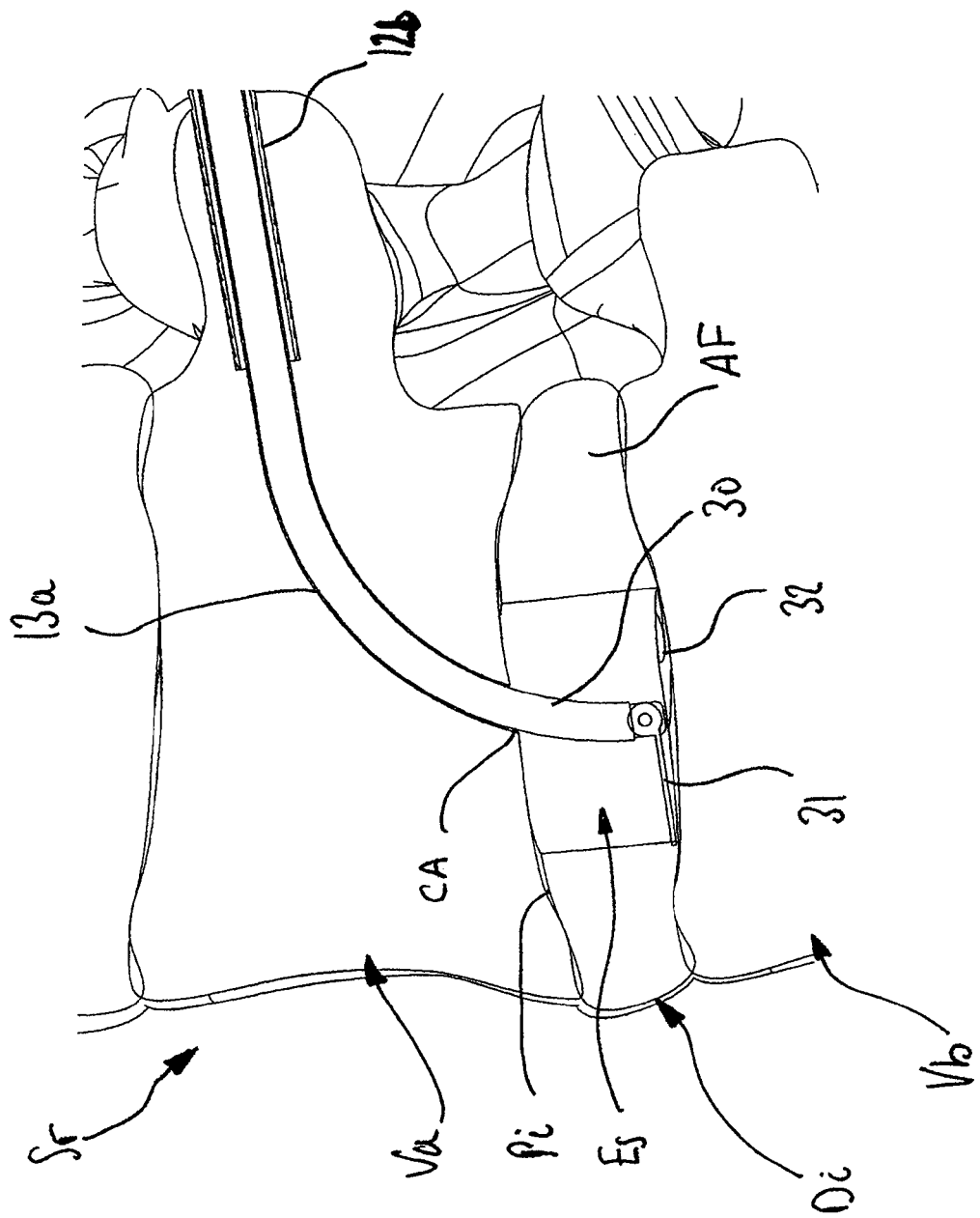

The surgeon inserts a flexible cutter or flexible impactor 16a into the curved guide tube or curved cannula 13a, and said cutter or impactor makes it possible to pierce the lower plate Pi of the overlying vertebra Va (FIG. 8).

After the flexible cutter 16a is removed, the surgeon inserts—under x-ray monitoring into the curved guide tube or curved cannula 13a—a device for flexible cutting or a flexible cutting rod 30 that comprises, for example, at its end, cutting tools or small retractable cutting blades 31, 32 that are actuated in rotation to reduce the tissues of the nuclear space Es into debris that can be evacuated via the bone channel of transpedicular guiding Ca (FIGS. 9 to 12).

Figure 13:
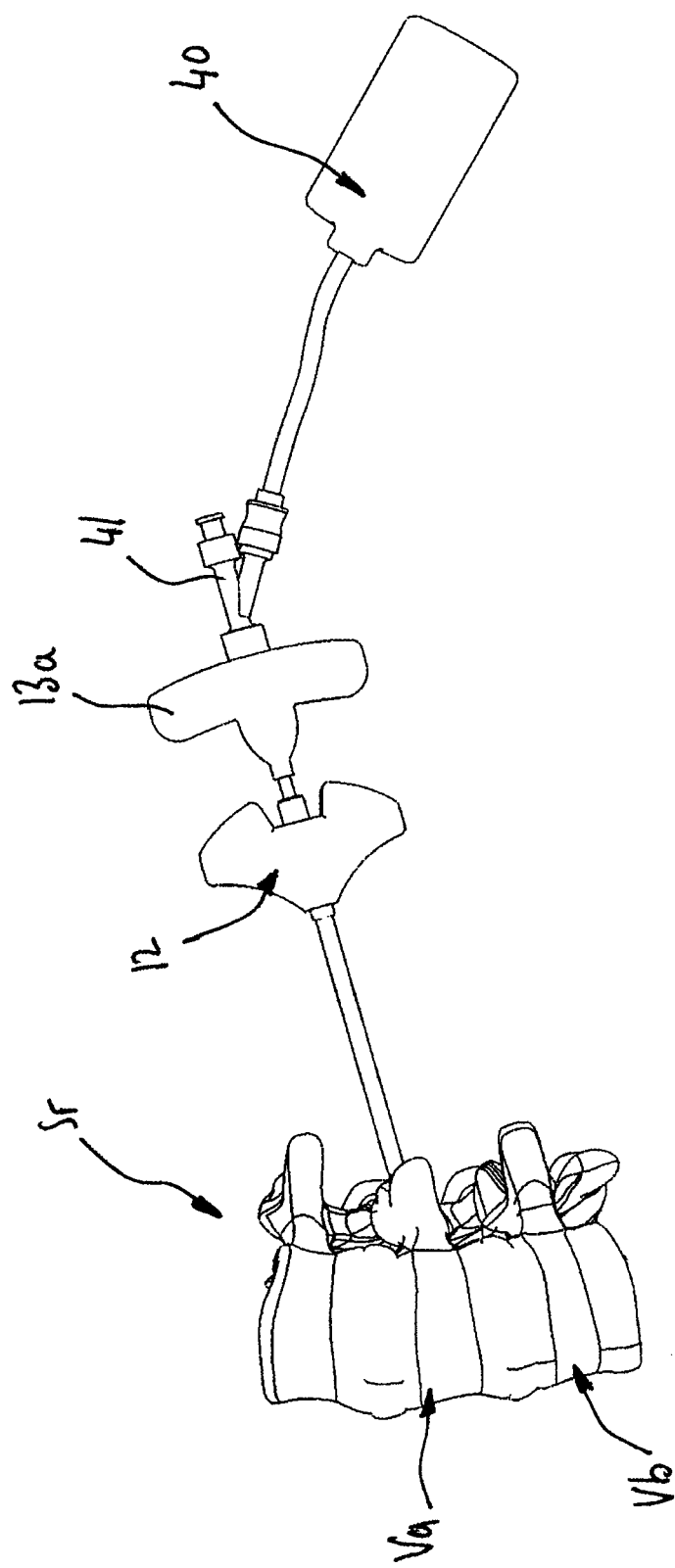

Under x-ray monitoring, the surgeon initiates cleaning of the nuclear space Es by means of a flexible cannula 42 that is inserted through the sealed connection 41 into the curved cannula 13a up to the interior of said nuclear space Es and connected to a system or pump 40 that makes possible the injection and aspiration of physiological liquid. The aspiration of the liquid via the system or pump 40 allows the entrainment of debris outside of the nuclear space Es (FIG. 13).

As soon as the nuclear space Es is created, emptied and cleaned, the surgeon can initiate the insertion of the nuclear implant 1 that consists of the filling element 2 that is formed by the wire 50 inside said space.

Through the connection 41 and into the curved guide tube or curved cannula 13a, the surgeon inserts a wire-guide flexible sheath 18 until the lower plate Pi of the overlying vertebra Va is reached to extend into the nuclear space Es. The flexible sheath 18 has an internal bore 18a that corresponds approximately to the diameter of the wire 50 that is to be inserted into the nuclear space Es (FIGS. 14, 15).

Figure 14:
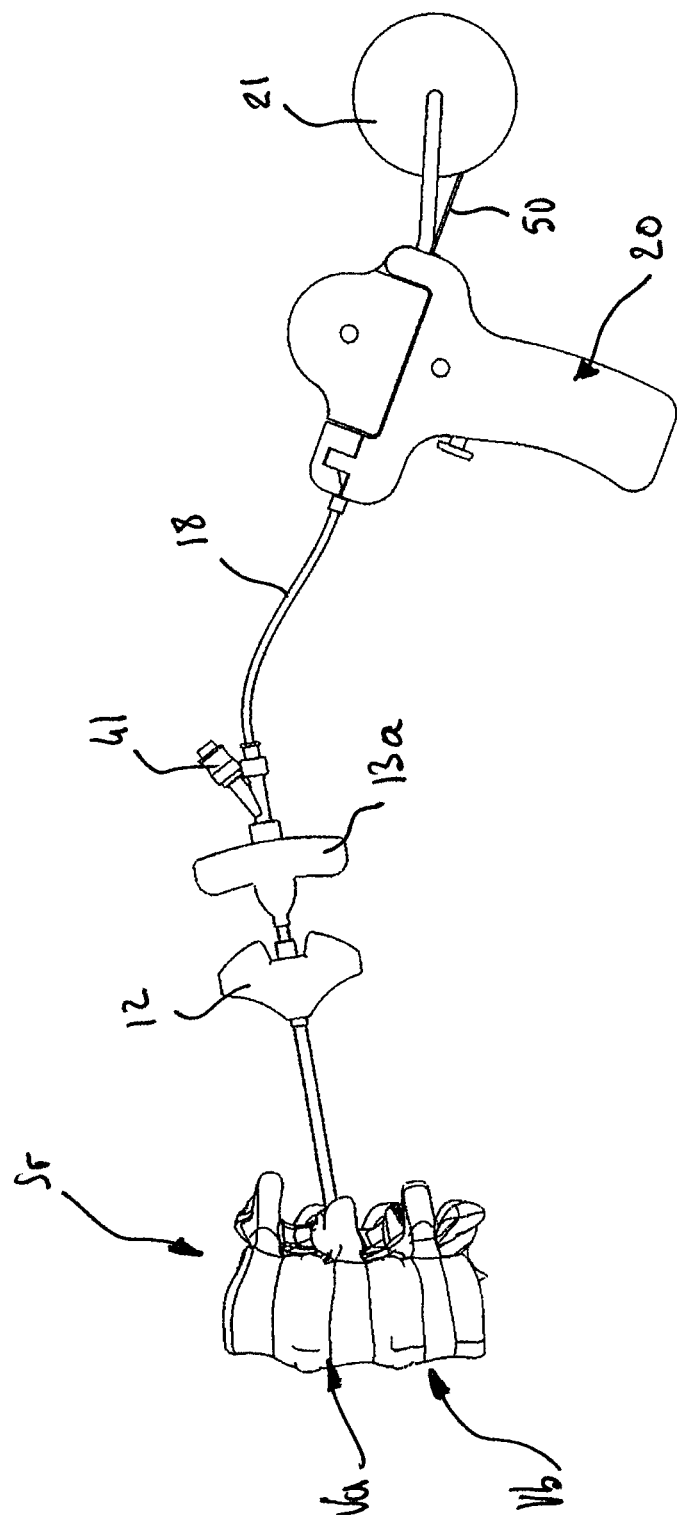
Figure 15:
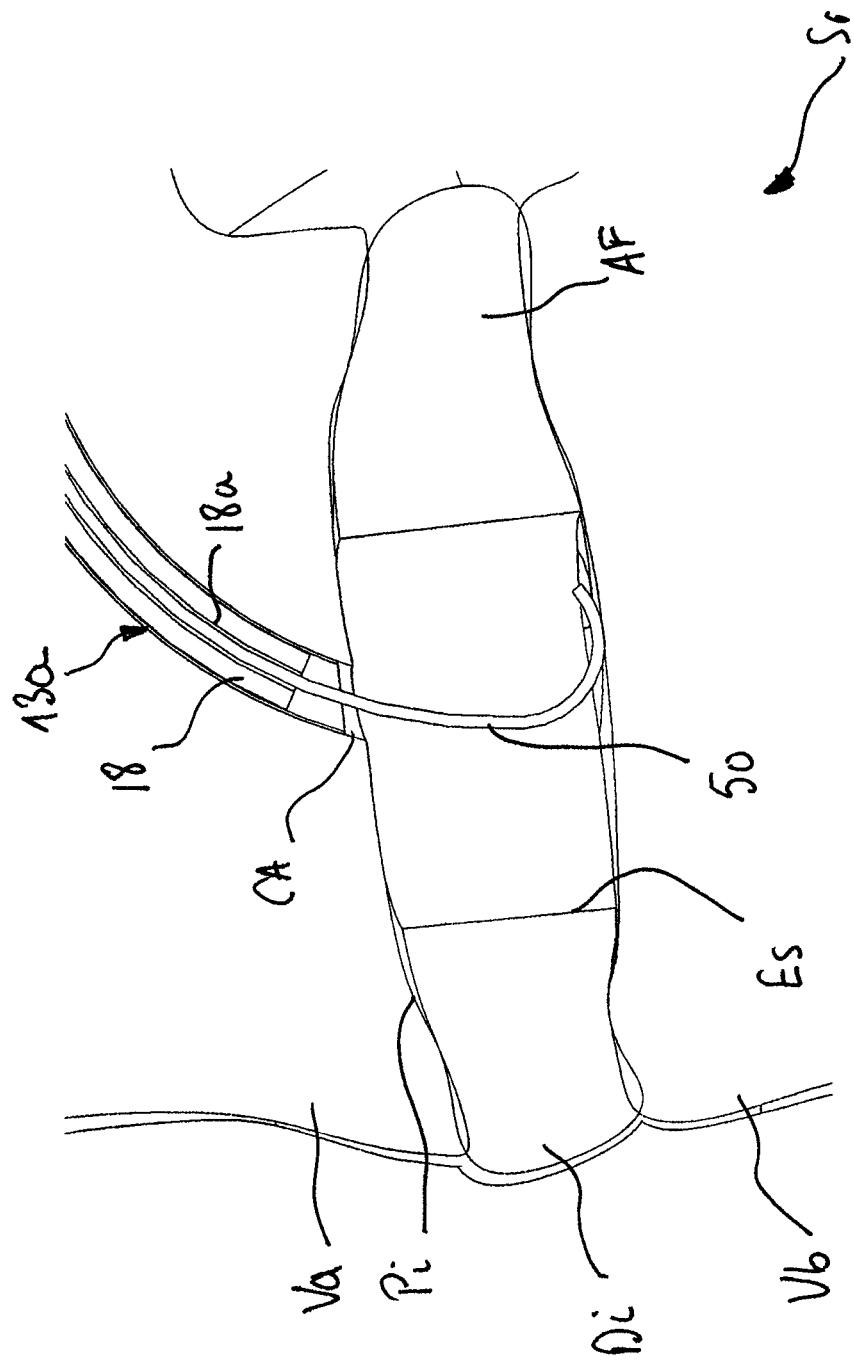

The surgeon connects the flexible sheath 18 by means of a "welding-system wire feed"-type insertion system that comprises, for example, a gun 20 that is equipped with an internal or external loader 21 in which an adequate length of wire 50 is wound (FIG. 14).

Figure 16:
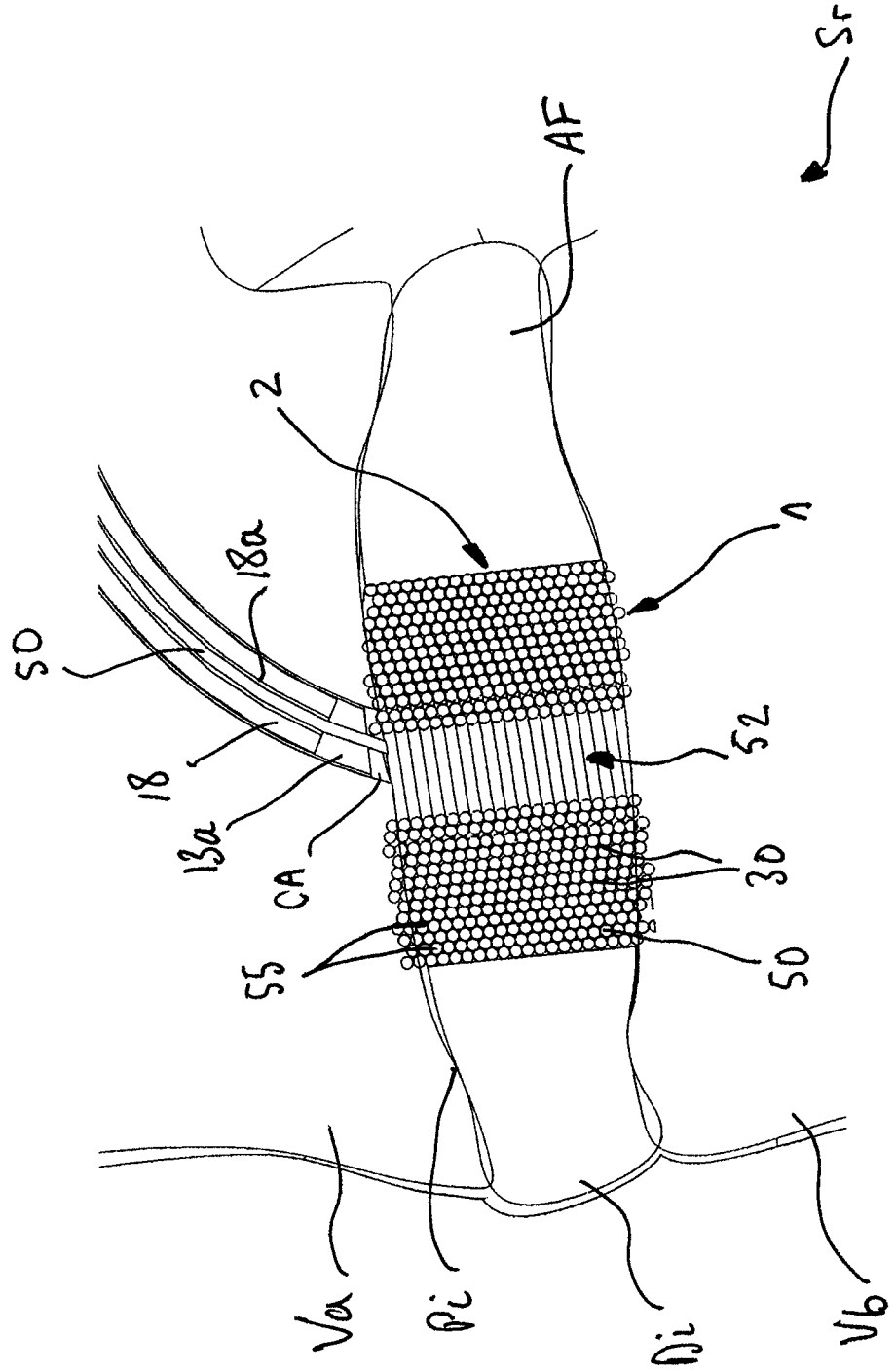

The surgeon activates the driving means of the gun 20 that causes the wire 50 inside the internal bore 18a of the flexible sheath 18 to be thrust up to the interior of the nuclear space Es that is provided in the intervertebral disk Di. A certain length of wire 50 is inserted into the nuclear space Es at a controlled speed. The continuous insertion of the wire 50 and its ring-shaped placement in the nuclear space Es are tracked under x-ray monitoring because the wire 50 is radio-opaque (FIGS. 15, 16). The wire 50 that is pushed in this way winds and covers the inside walls of the "annulus fibrosus" (AF) by coiling up. Actually, the wire 50 having a certain rigidity curves by the buckling effect and is placed in a ring in the nuclear space 1 by forming rows of contiguous coils 55 over the entire height of said space. By coiling up, the wire 50 forms a ring with an essentially vertical axis relative to the plates of the vertebrae Va, Vb inside the nuclear space Es. The ring of coils 55 delimits an internal central space 52 that can be filled by additional products that are introduced prior to the procedure such as another wire 51 or a product 53 that can be a gel, a pasty product, a fiber-based product, an injectable viscoelastic material or by the formation of a post-operative fibrosis that is promoted by the vascularization due to the transpedicular access.

The surgeon removes the flexible sheath 18, the insertion system 20, the curved guide tube or curved cannula 13a, and the guide tube or straight cannula 12 of the bone channel Ca.

Figure 17:
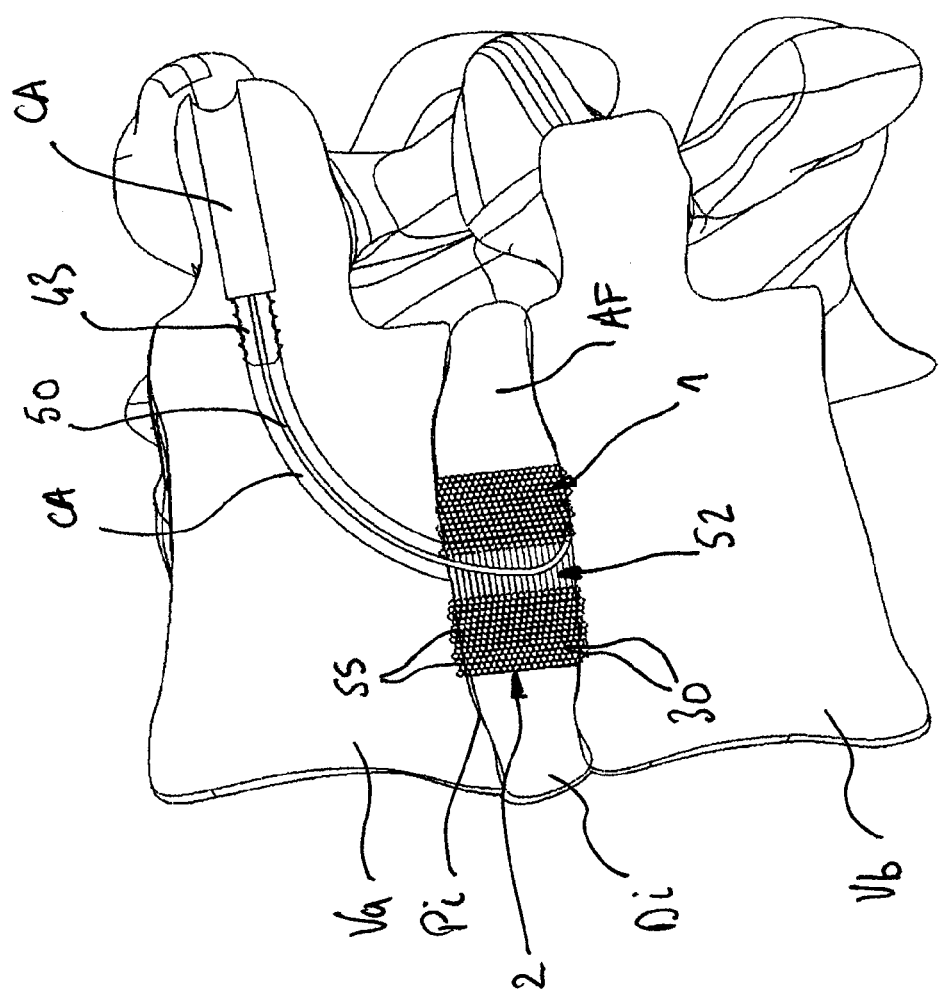

The surgeon attaches the end of the wire 50 that constitutes the ring to the vertebra Va inside the bone channel Ca by means of attachment means or by a seal 43 that also make(s) it possible to seal said bone channel. The wire 50 thus makes integral the nuclear implant 1 with the vertebra Va to preclude the potential migration problems (FIG. 17).

Insertion of the Nuclear Implant 1 into a Wire 50 by a Pathway of Transpedicular Access at the Level of the Underlying Vertebra Vb of a Spine Segment Sr (FIGS. 19 to 33)

Figure 19:
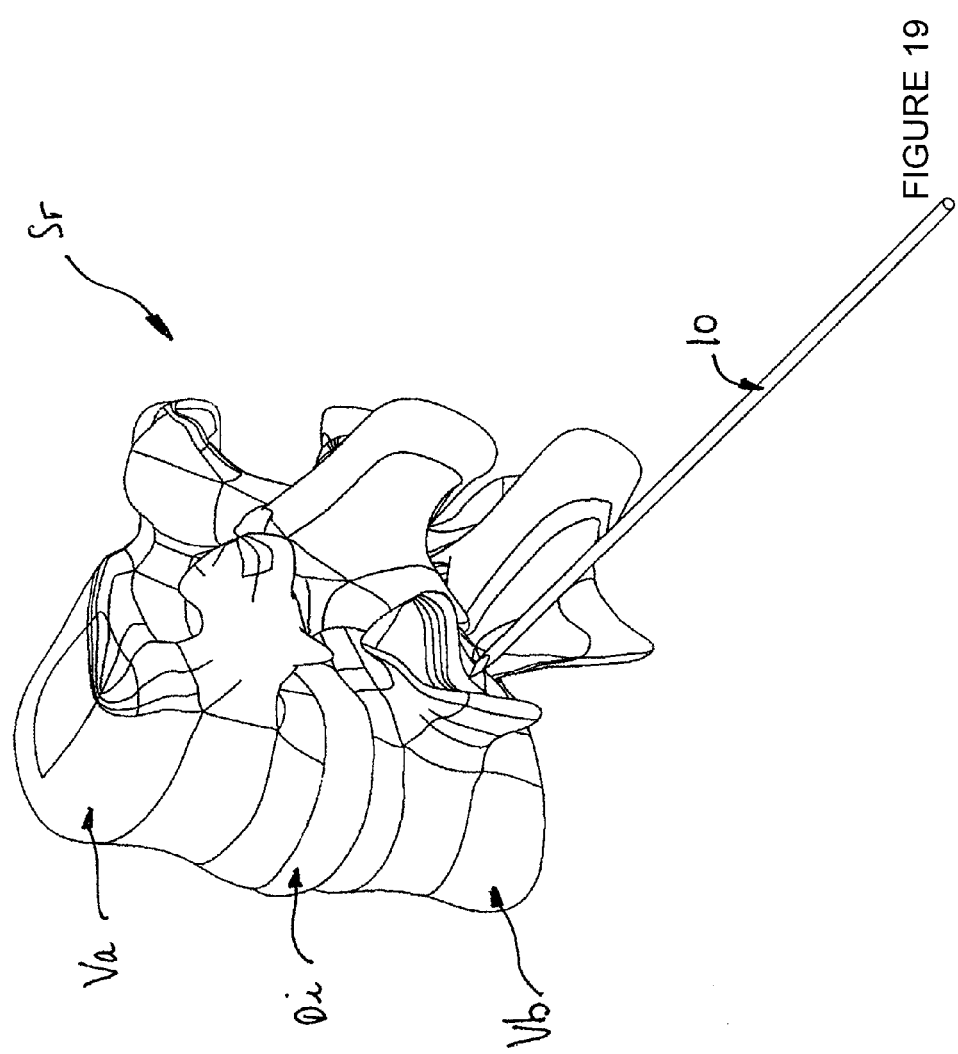
FIGS. 19 to 33 are views that show another embodiment of the various stages that allow the insertion of the nuclear implant by a pathway of transpedicular access at the level of the underlying vertebra Vb of a spine segment Sr according to this invention.

Thus, the pedicular view, the nucleotomy of the intervertebral disk Di, and the insertion of the nuclear implant 1 are conducted in the following manner by the surgeon:

The surgeon positions and inserts a guide pin 10 under x-ray monitoring into the pedicle of the underlying vertebra Vb of the spine segment Sr (FIG. 19).

Figure 20:
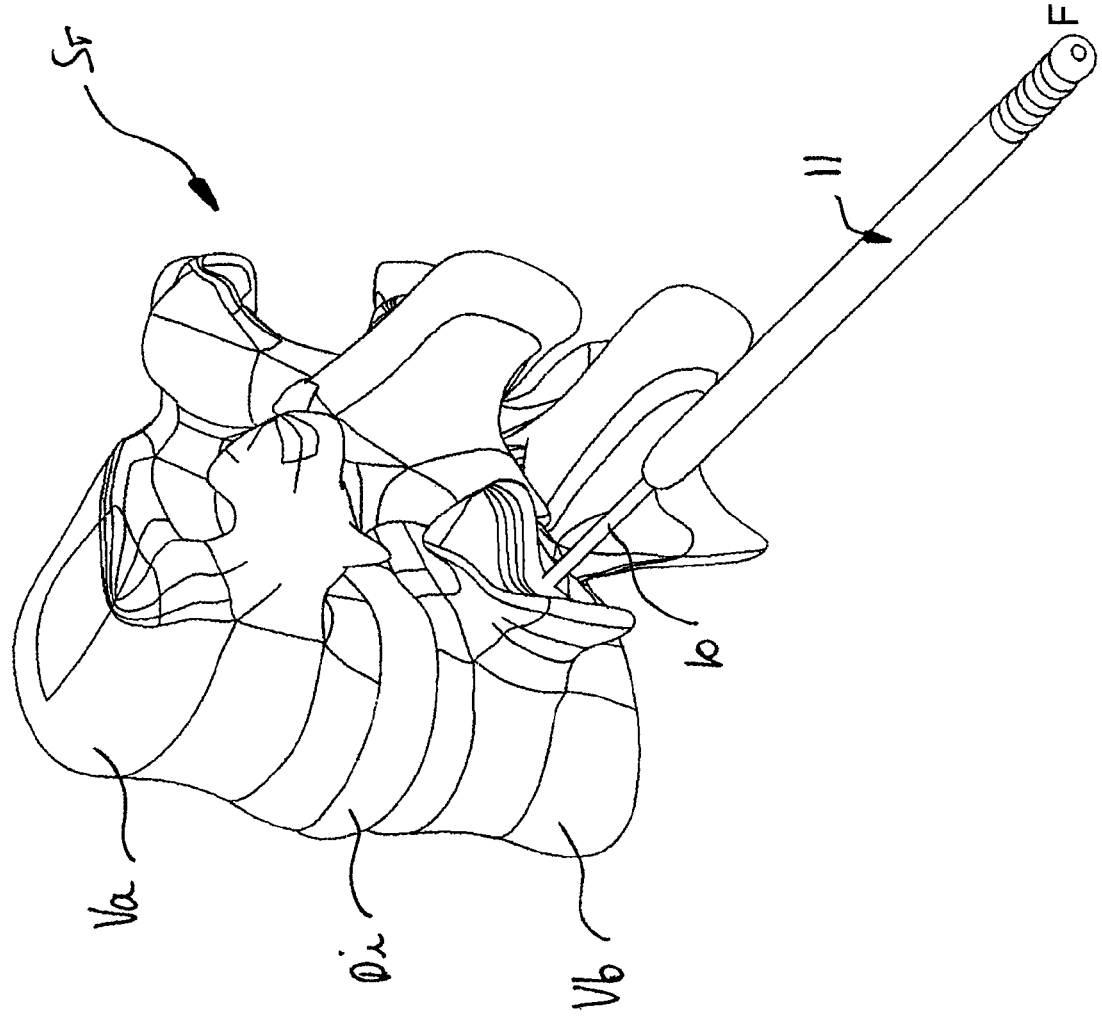

The surgeon threads a plug 11 onto the guide pin 10 to reach the pedicle (FIG. 20).

Figure 21:
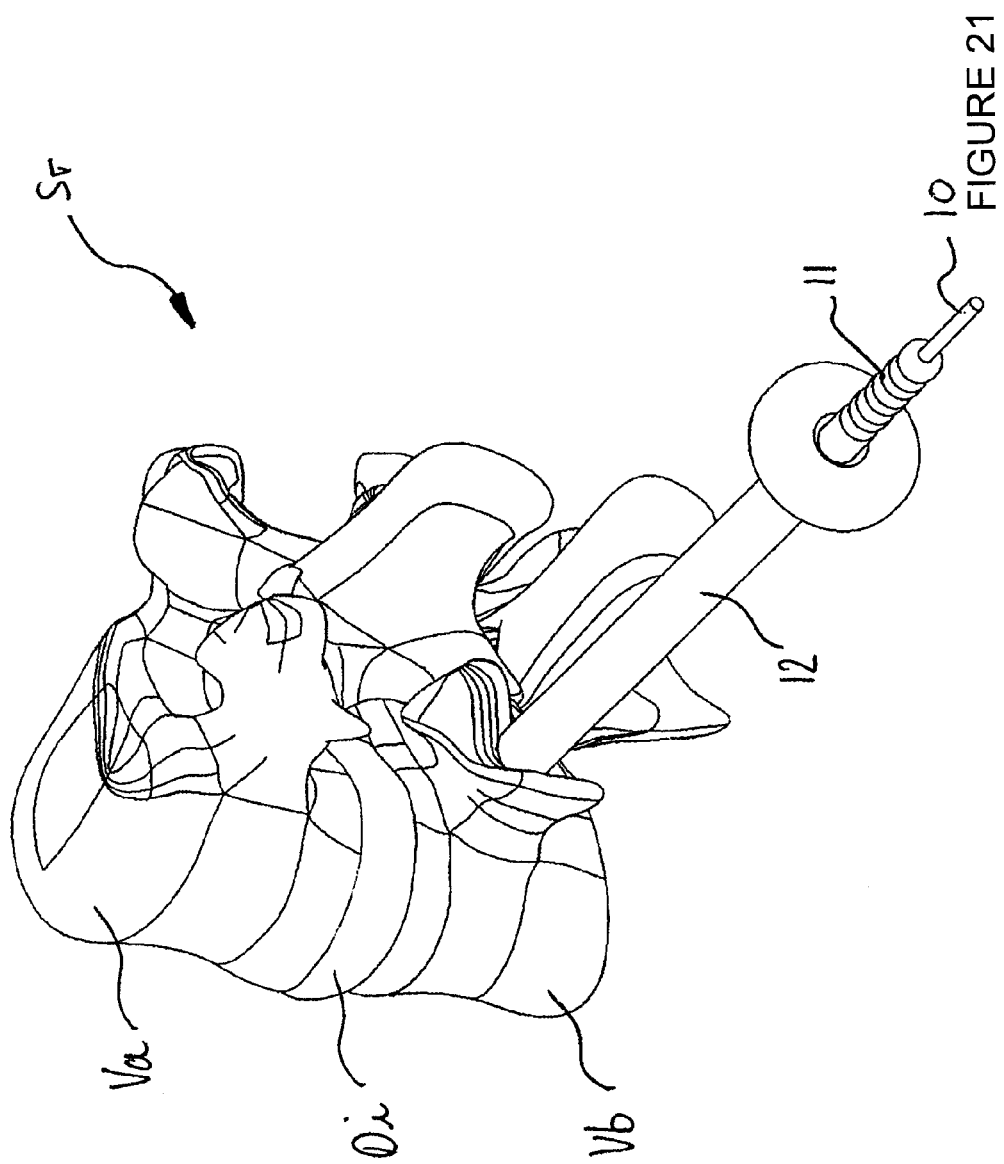
Figure 22:
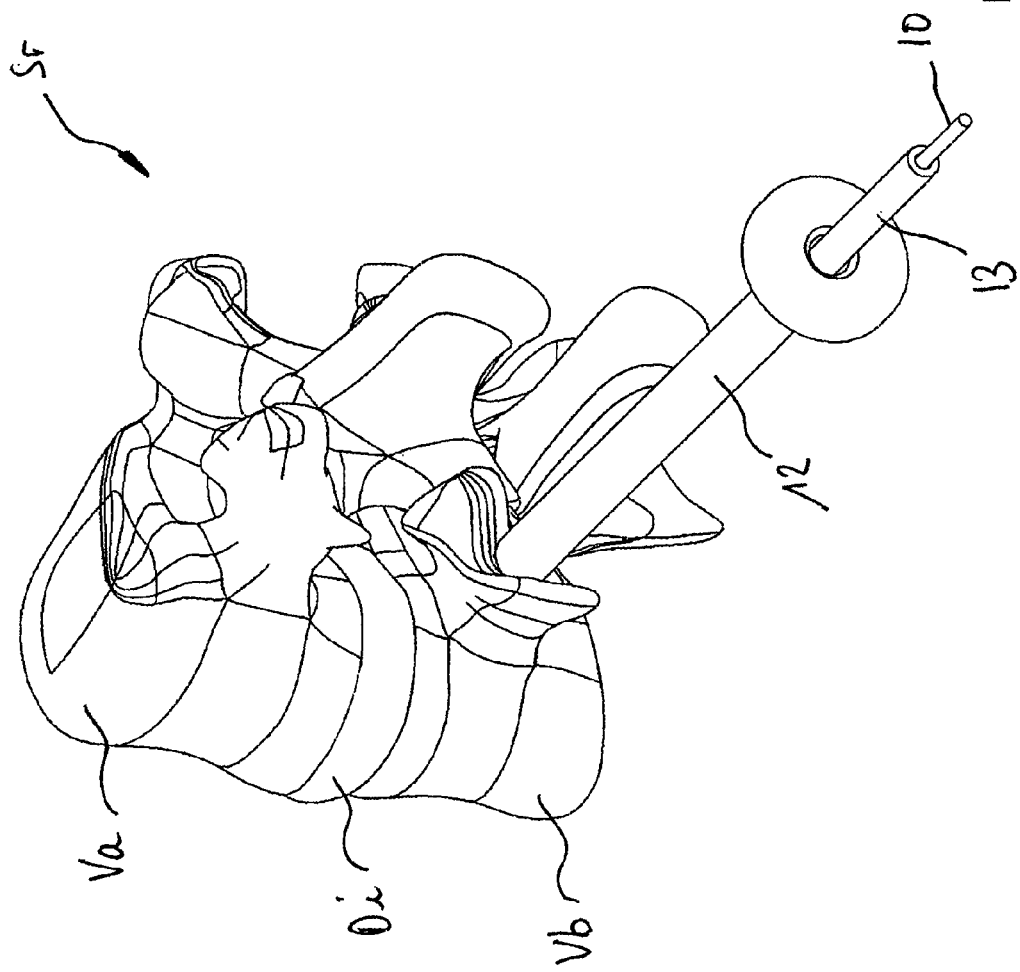
Figure 23:
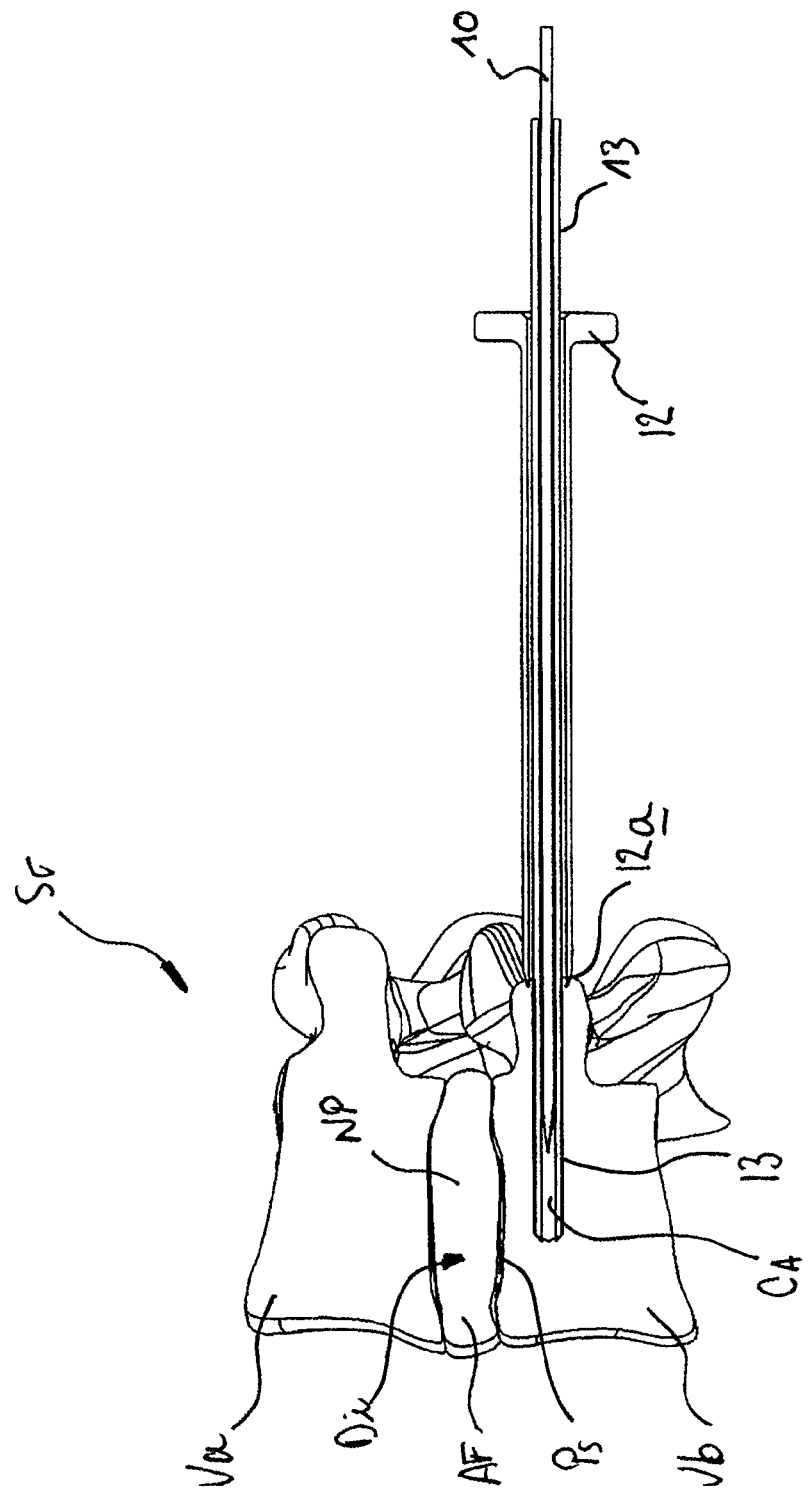

On the plug 11, the surgeon positions a guide tube or straight cannula 12 that is provided at its end with points 12a that allow an anchoring into the body of the underlying vertebra Vb (FIGS. 21 to 23).

Figure 24:
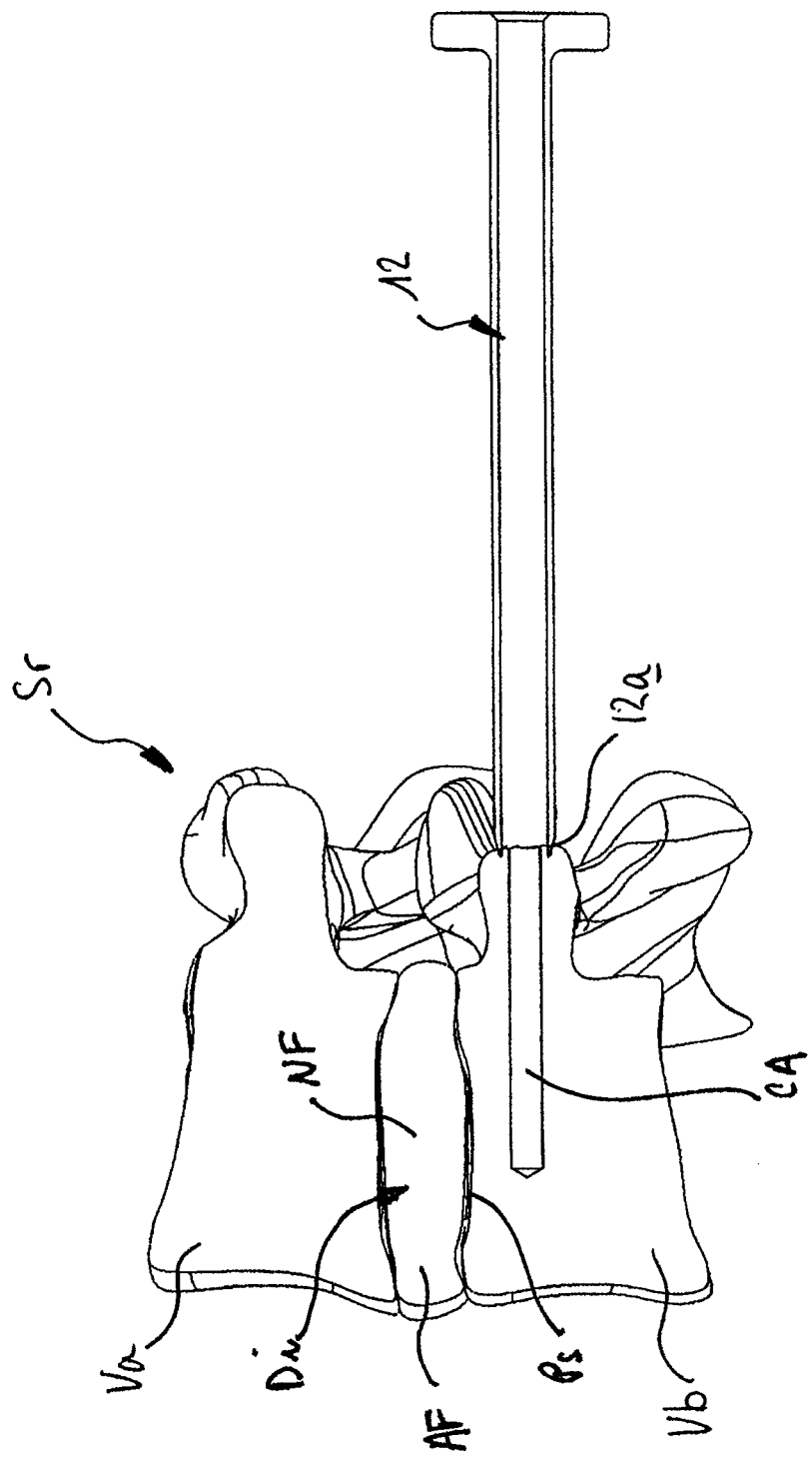

The surgeon removes the plug 11 and inserts—into the guide tube or straight cannula 12—a straight cannula bit 13 that makes it possible to provide in the body of the vertebra a bone channel for transpedicular guiding Ca up to below the upper plate Ps of the underlying vertebra Vb (FIGS. 23, 24).

Figure 25:
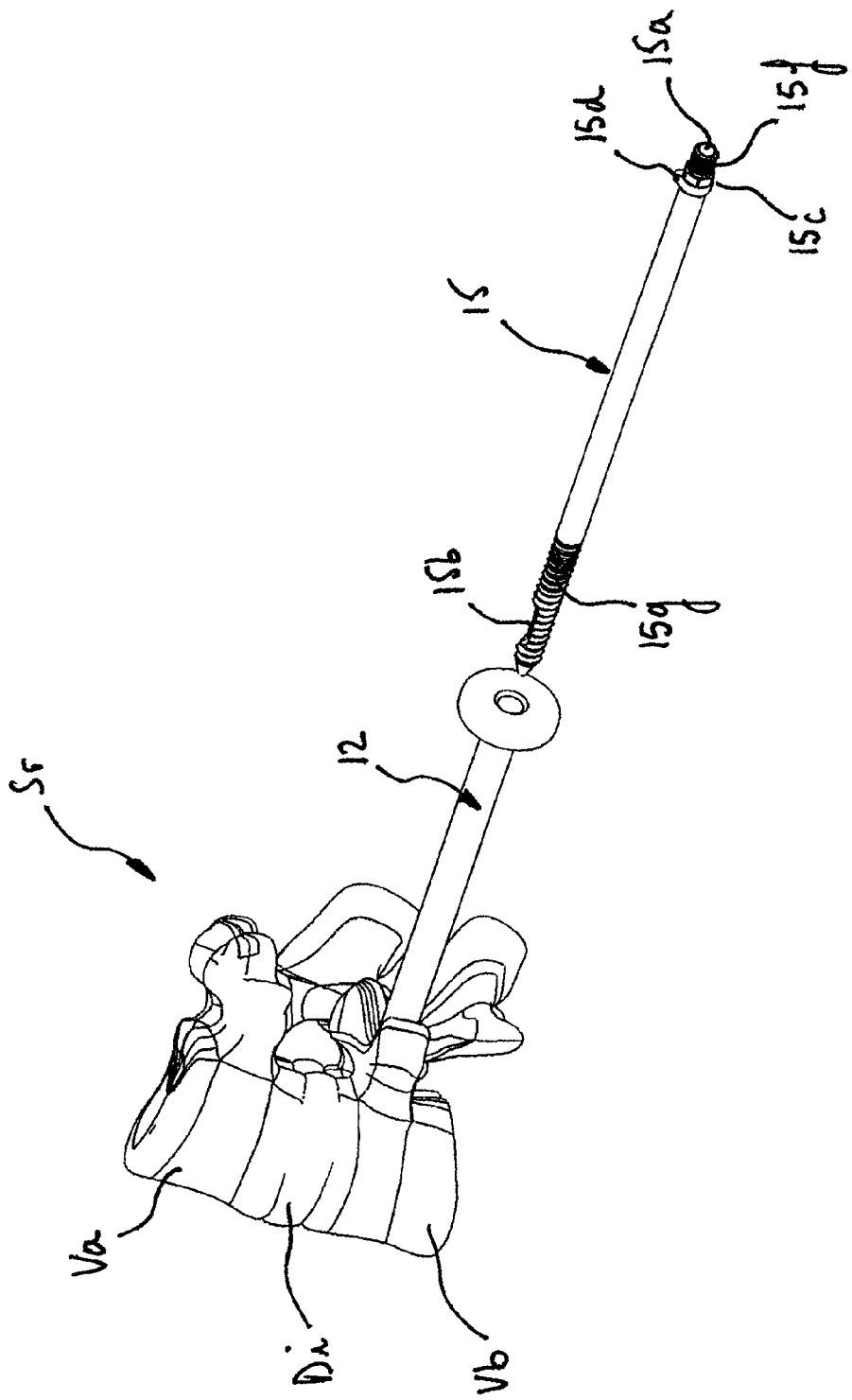

The surgeon removes the cannula bit 13 and the pin 10 to insert into the bone channel Ca a cannula 15 that is provided at one of its ends with a threading 15g that ensures its bone anchoring. This threaded cannula 15 has a lower channel 15a that ends by a lateral outlet 15b that is designed to reach to the upper plate Ps of the underlying vertebra Vb. The screwing of the cannula 15 is carried out under x-ray monitoring that allows the marking of the channel 15a that is to be placed at the level of the center of disk Di. The cannula 15 comprises one end 15c that goes beyond the level of the skin so that the entrance to the channel 15a is easily accessible. The end of the cannula 15 consists of a head 15c whose outside profile makes possible the driving in rotation of said cannula. The head 15c is integral on its periphery with a reference index 15d that makes it possible for the surgeon to visualize the position of the lateral outlet 15b of the inner channel 15a inside the underlying vertebra Vb. The head 15c comprises a threaded extension 15f that ensures the connection of the cannula 15 with a wire guide sheath 18 (FIG. 25).

Figure 26:
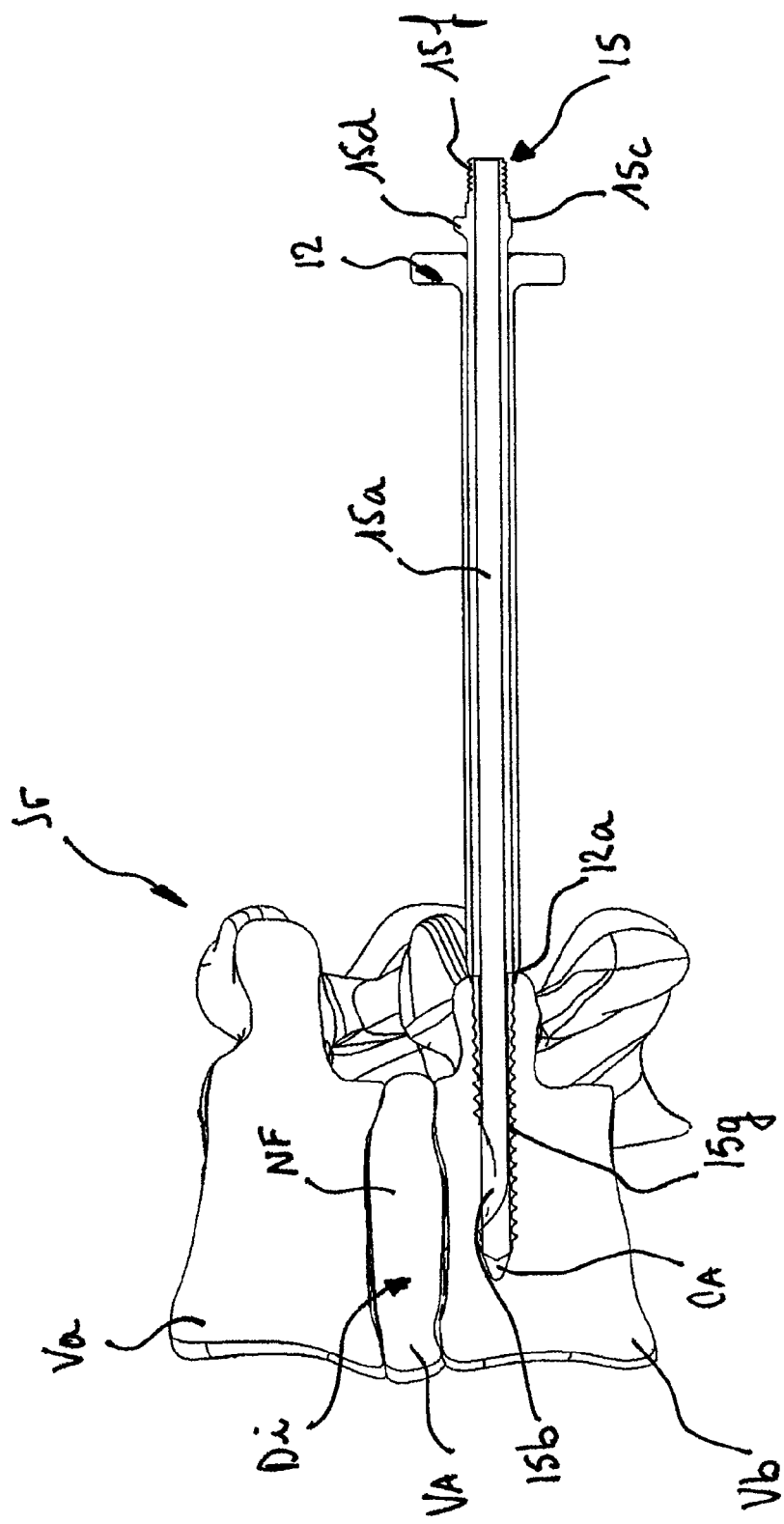

The surgeon positions the lateral orifice 15b of the threaded cannula 15 in the direction of the upper plate Ps of the underlying vertebra Vb to be able to reach the lower surface of the intervertebral disk Di (FIG. 26).

Figure 27:
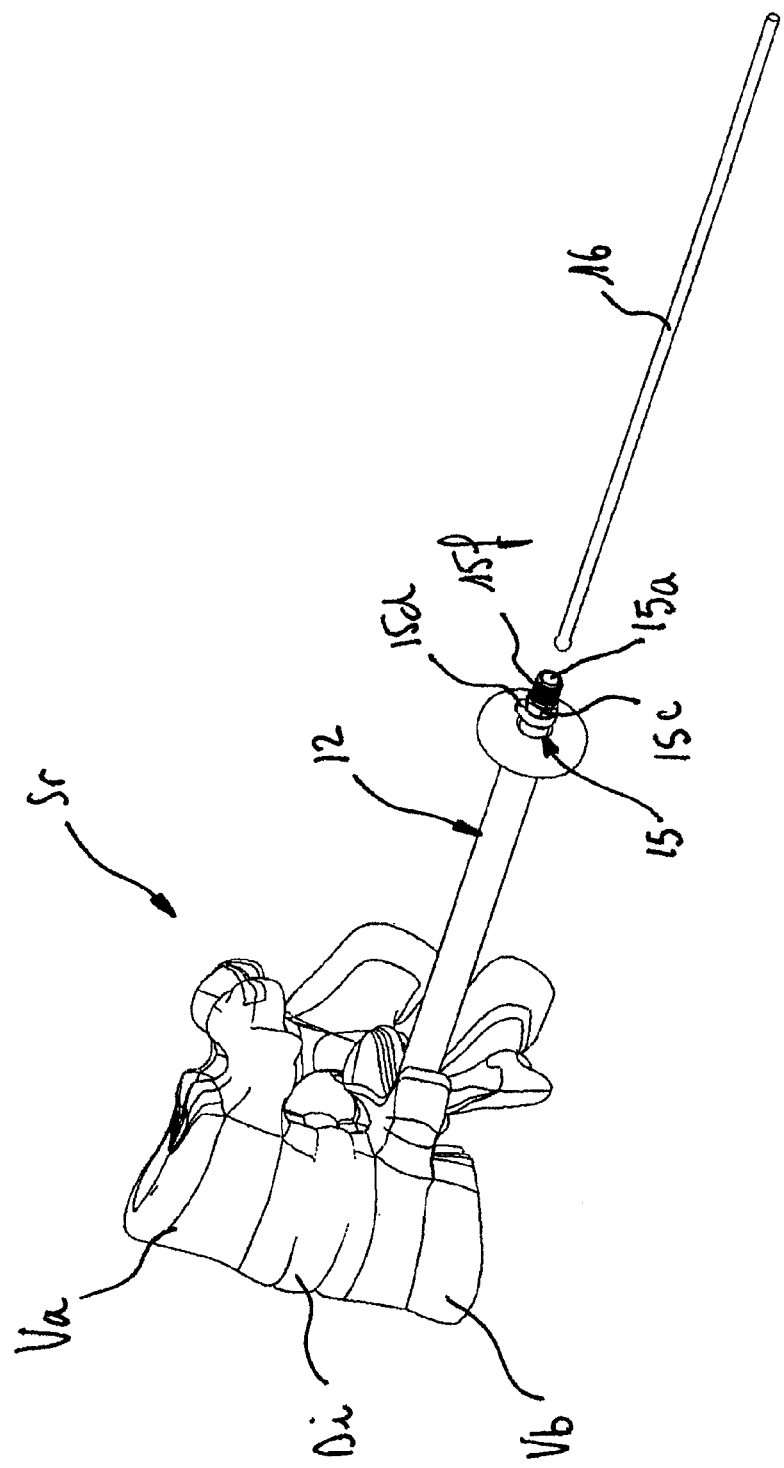
Figure 28:
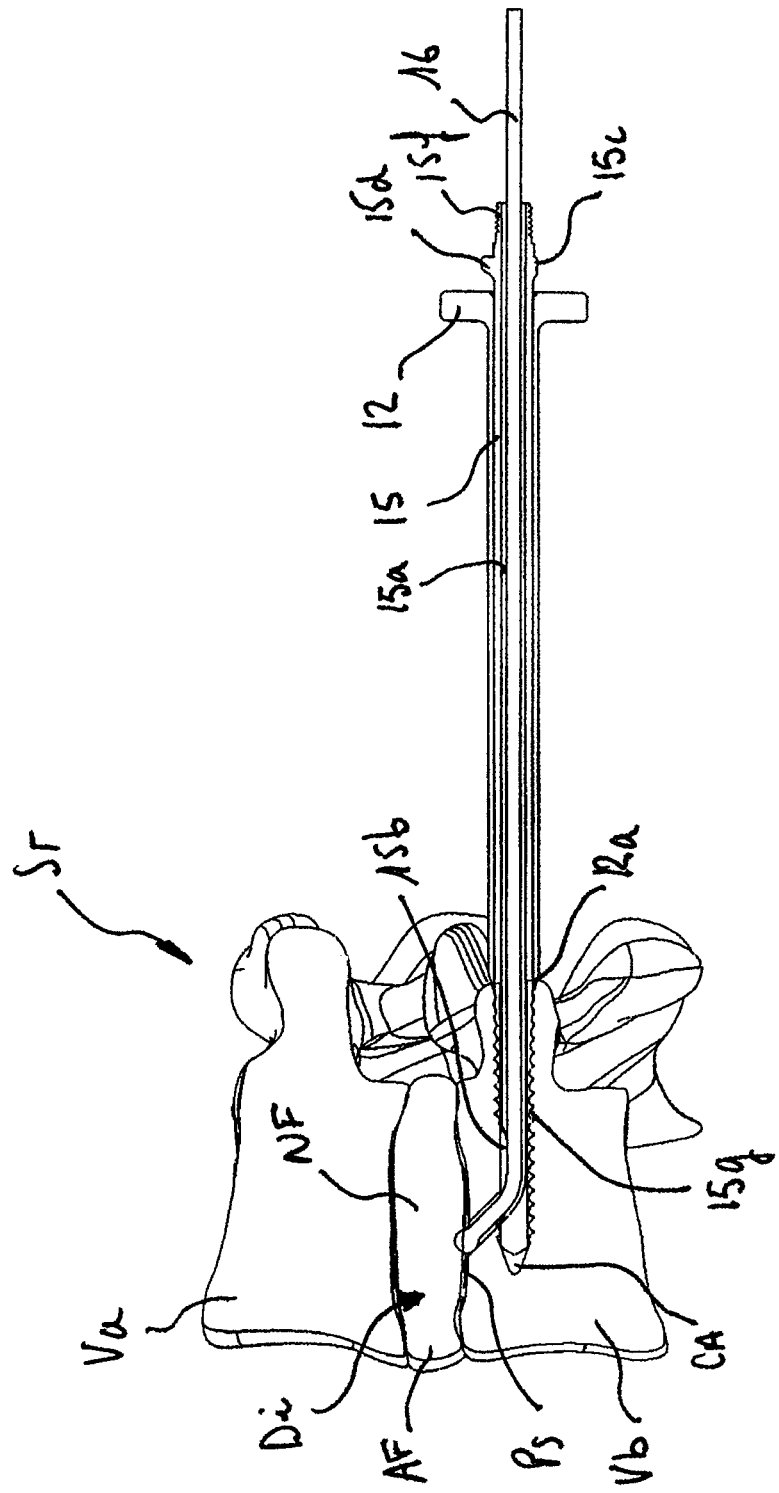

The surgeon perforates the upper plate Ps of the underlying vertebra Vb and the lower surface of the intervertebral disk Di by means of a bit or a flexible square point 16 that is inserted inside the bore 15*a* of the threaded cannula 15 to reach the internal structure that is designated "nucleus pulposus" (NP) of said intervertebral disk Di (FIGS. 27, 28).

Figure 29:
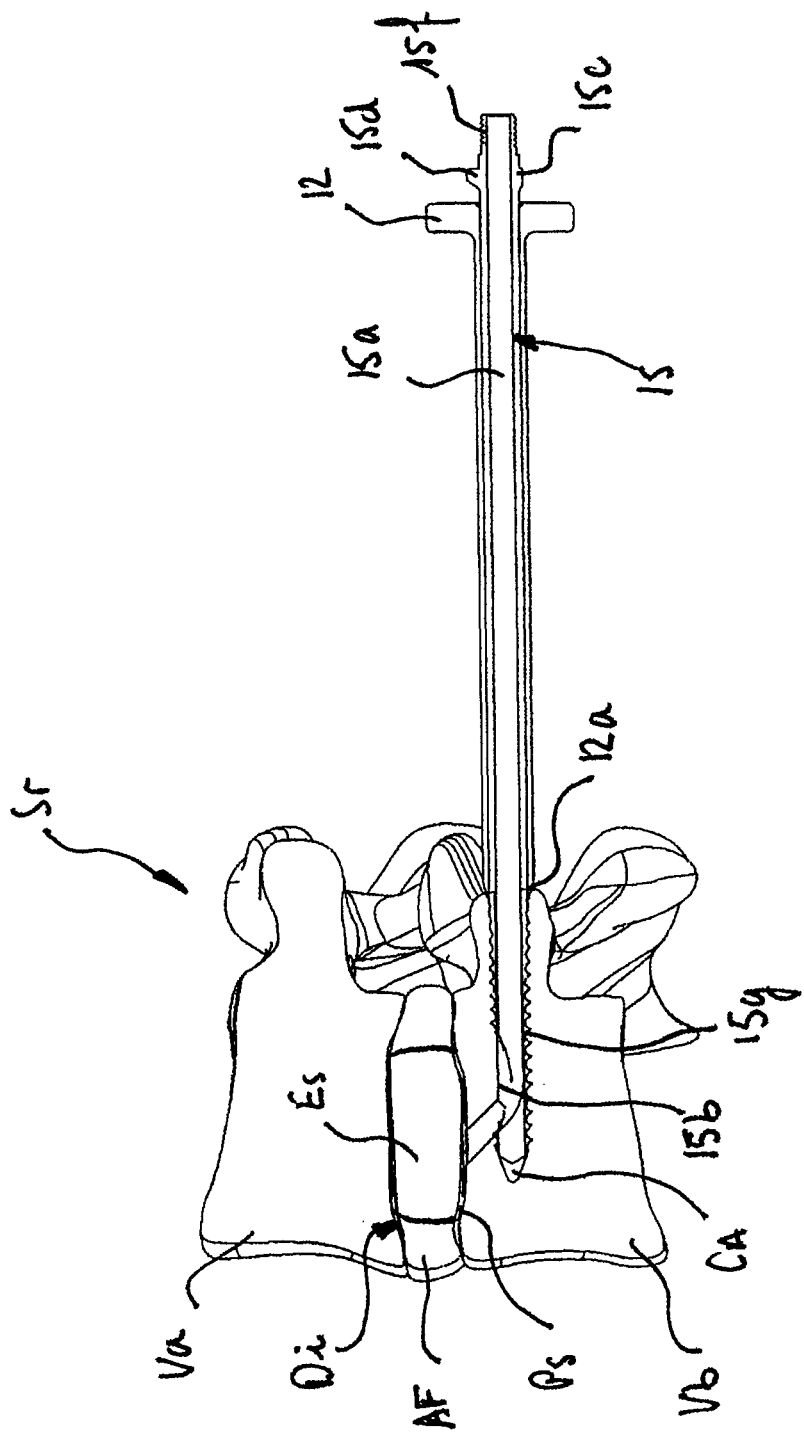

The surgeon then initiates the nucleotomy of the intervertebral disk Di. The percutaneous nucleotomy consists in eliminating, in a controlled manner, the maximum "nucleus pulposus" (NP) of the intervertebral disk Di through the threaded cannula 15. For this purpose, by means of the threaded cannula 15 and into the intervertebral disk Di, the surgeon inserts an extraction device, not shown, with a small diameter and comprising, for example, a laser fiber, an optical fiber connected to a camera, an irrigation hole, and an aspiration hole. The extraction device comprises a mechanism that makes it possible for the surgeon to orient the laser fiber to carry out the elimination of the "nucleus pulposus" (NP) in a precise manner and under monitoring of the camera. The laser beam vaporizes the tissues to be eliminated, and the irrigation system that is integrated into the extraction device makes it possible to maintain a controlled temperature to avoid affecting the tissues surrounding the work zone and to evacuate the products of the nucleotomy by the aspiration hole of the extraction device. The nucleotomy is carried out, according to the habits of each surgeon, manually, with laser or by coblation. The surgeon removes the "nucleus pulposus" (NP) so as to release a nuclear space Es (FIG. 29).

As soon as the nuclear space Es is created, emptied and cleaned, the surgeon can initiate the insertion of the nuclear implant 1 that consists of the filling element 2 that is formed by the wire 50 inside said space.

Figure 30:
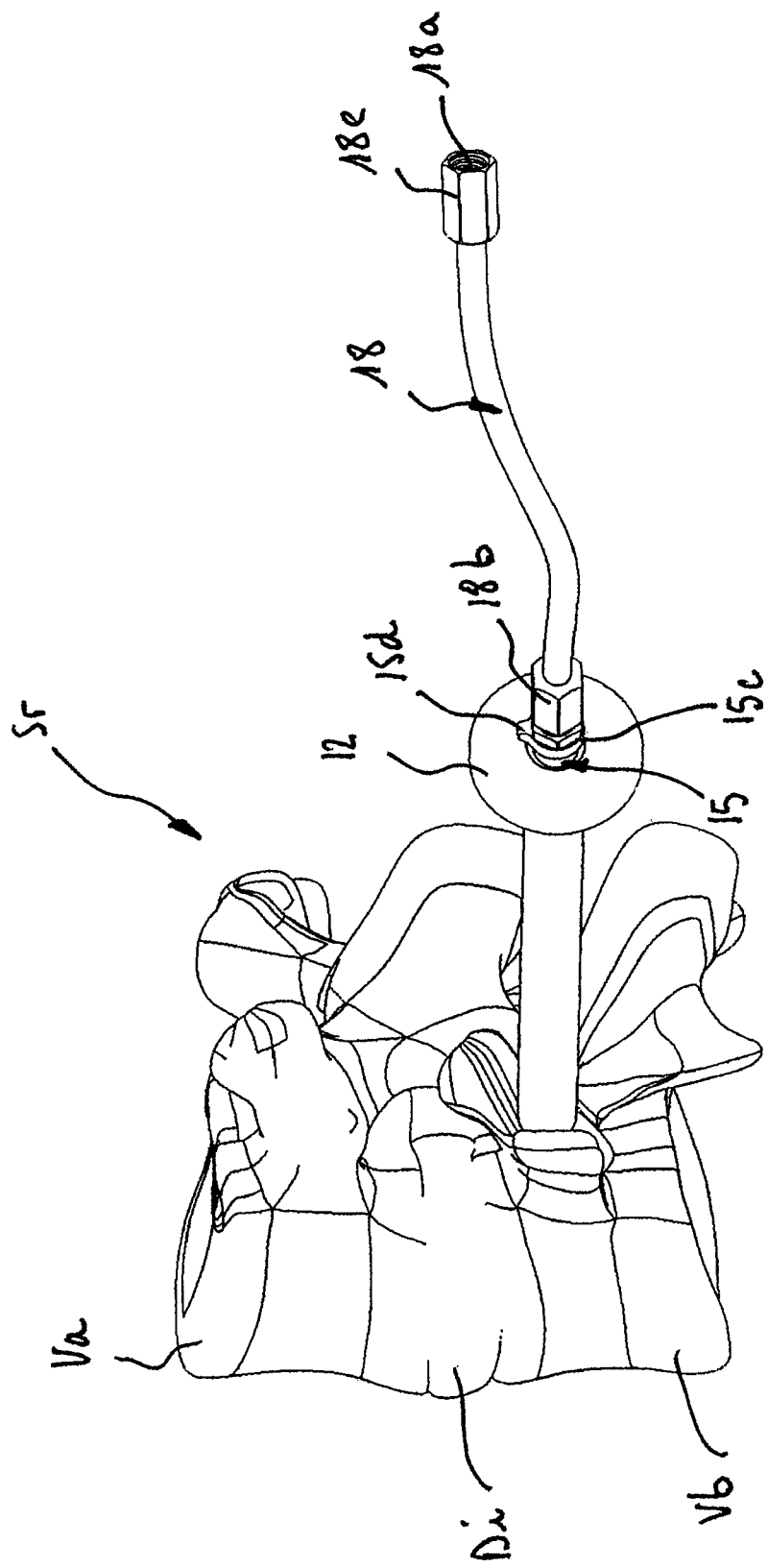
Figure 31:
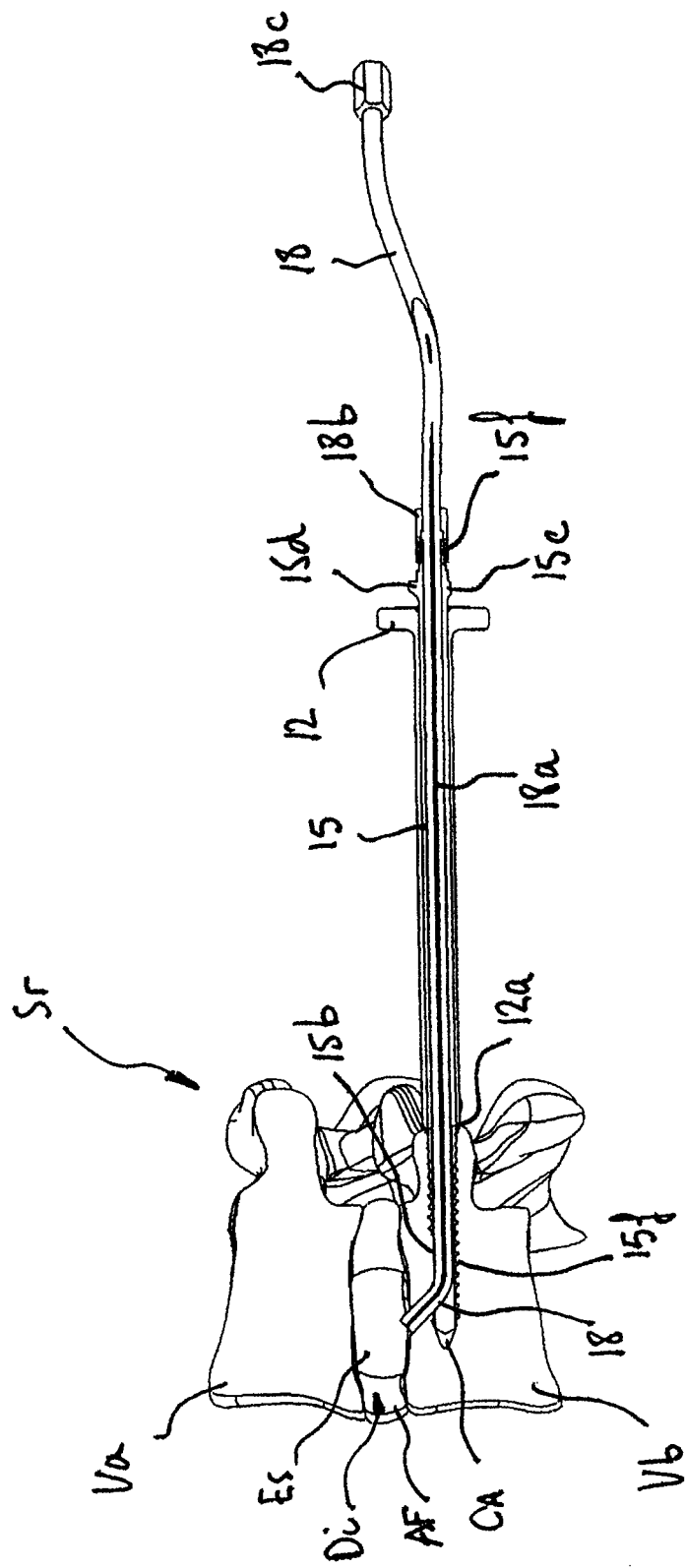

The surgeon inserts a wire-guide flexible sheath 18 into the threaded cannula 15 until it reaches the upper plate Ps of the underlying vertebra Vb, where it extends into the inside of the nuclear space Es. The flexible sheath 18 has an internal bore 18*a* that corresponds essentially to the diameter of the filling element 2 that can consist of a wire 50 that is to be inserted into the nuclear space Es. The flexible sheath 18 is attached to the threaded cannula 15 as soon as its free end slightly penetrates the nuclear space Es that is provided in the intervertebral disk Di by means of a first connection 18*b*. The flexible sheath 18 has as its function to facilitate the guiding of the wire 50 until it is in the nuclear space Es that is released by the nucleotomy (FIGS. 30, 31).

Figure 32:
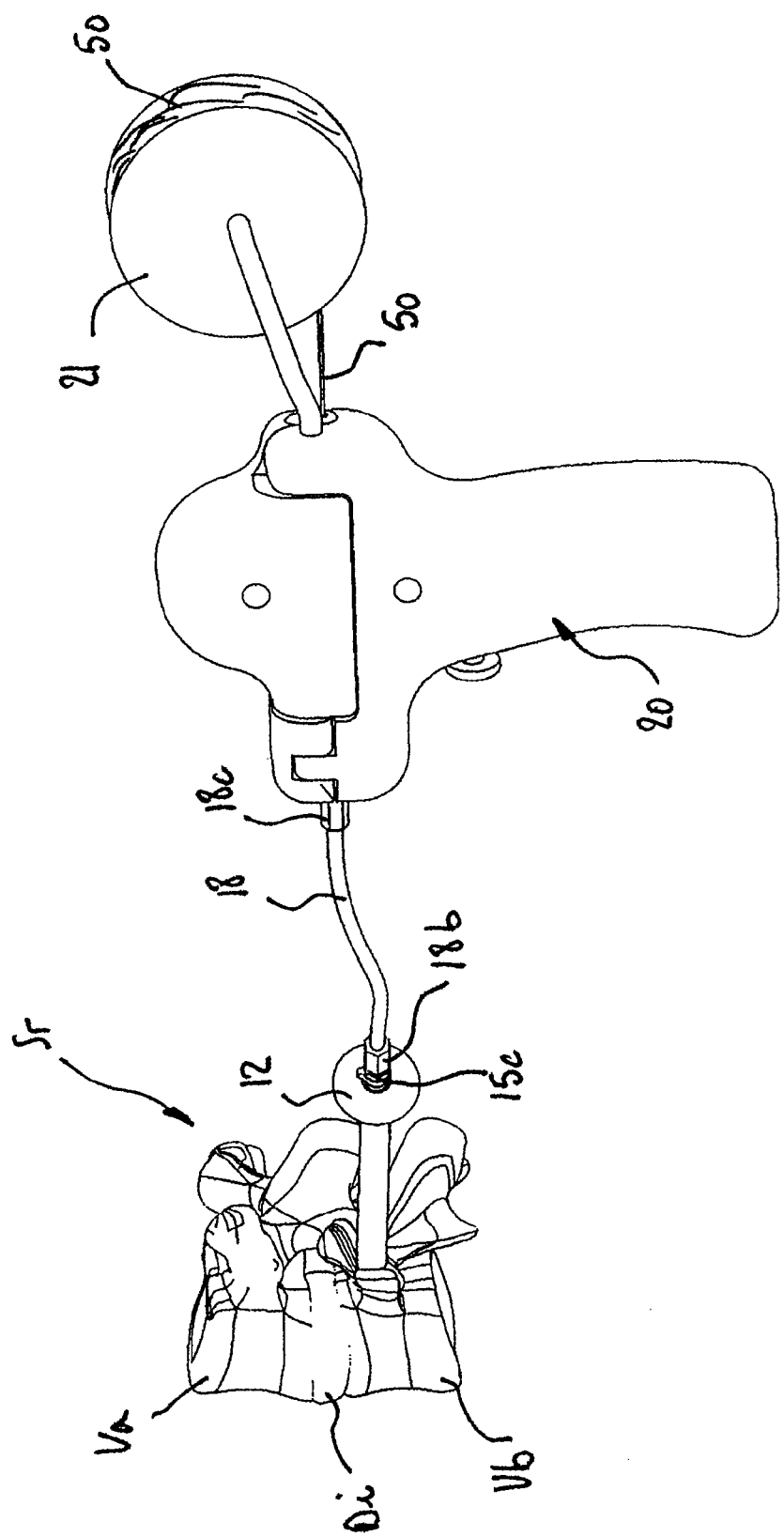

The surgeon connects the flexible sheath 18 by means of a "welding-system wire feed"-type insertion system that comprises, for example, a gun 20 that is equipped with an internal or external loader 21 in which an adequate length of wire 50 is wound (FIG. 32).

Figure 33:
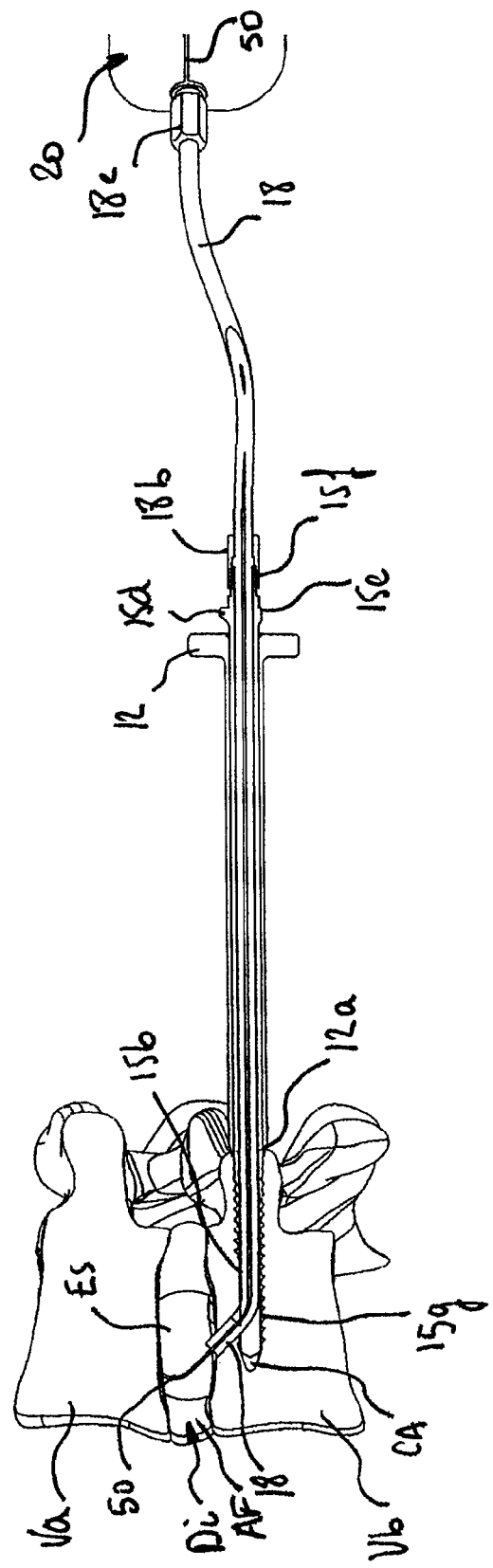

The surgeon activates the driving means of the gun 20 that cause the wire 50 inside the internal bore 18*a* of the first flexible sheath 18 to be thrust up to the interior of the nuclear space Es that is provided in the intervertebral disk Di. A certain length of wire 50 is inserted into the nuclear space Es at a controlled speed. The continuous insertion of the wire 50 and its ring-shaped placement in the nuclear space Es are tracked under x-ray monitoring because the wire 50 is radio-opaque (FIG. 33).

The surgeon removes the flexible sheath 18, the insertion system 20, the threaded cannula 15, and the guide tube or straight cannula 12 of the bone channel Ca.

The surgeon attaches the end of the wire 50 that constitutes the ring to the vertebra Vb inside the bone channel Ca by means of attachment means or by a seal 43 that also makes it possible to seal said bone channel. The wire 50 thus makes integral the nuclear implant 1 with the vertebra Vb to preclude the potential migration problems.

Figure 34:
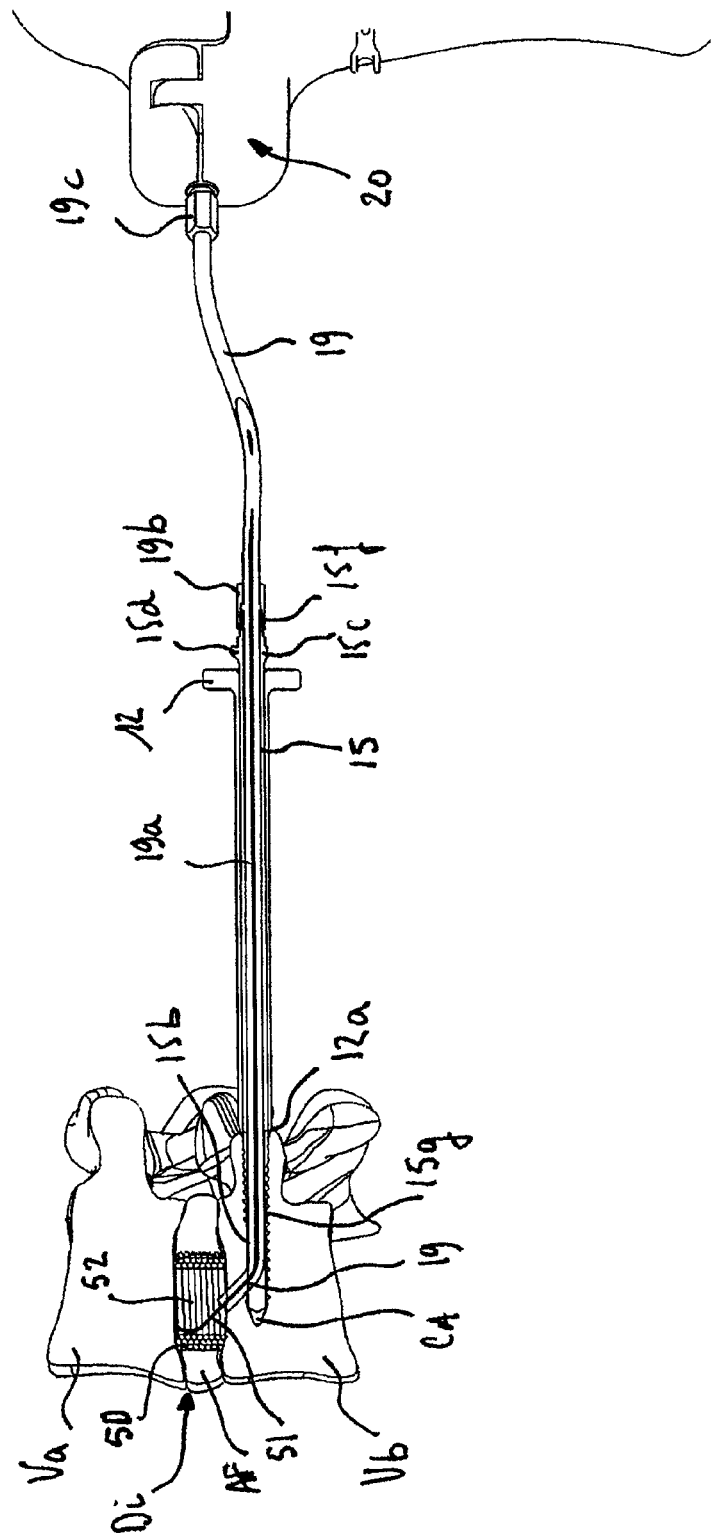
FIGS. 34 to 36 are views that illustrate the insertion of a second wire inside the central internal space that is formed by the ring of the first wire of the nuclear implant by a pathway of transpedicular access according to this invention.

Nuclear Implant 1 with Two Wires 50, 51 (FIGS. 2, 34, 36)

In the case where the filling element 2 is formed by, for example, a wire ring 50 that delimits a central internal space 52, the latter can be filled by another wire 51 that is arranged either in a ring or in a ball. The filling element 2 is formed by, for example, a wire ring 50 that partially fills the nuclear space Es and makes it possible to produce a pseudo-annulus, whose function will be to protect and reinforce the "annulus fibrosus" (AF) and to prevent the risks of subsequent formation or degradation of the "annulus fibrosus" (AF).

Thus, after the removal of the flexible sheath 18,

The surgeon inserts another wire-guide flexible sheath 19 until it reaches the plate of the vertebra, where it extends into the inside of the nuclear space Es (FIG. 34).

The surgeon connects the other wire-guide flexible sheath 19 by connections 19*b*, 19*c*, to the barrel of the gun 20 that is provided with another loader 22 around which is wound a second wire 51 whose outside diameter is different from that of the first wire 50 (FIG. 34).

The surgeon activates the driving means of the gun 20 that cause the wire 51 inside the other flexible sheath 19 to be thrust up to the interior of the nuclear space Es that is provided in the intervertebral disk Di. A certain length of wire 51 is inserted into the central internal space 52 that is delimited by the wire 50 that is arranged in a ring. The continuous insertion of the wire 51 and its placement in the shape of a ring or a ball are tracked under x-ray monitoring because the wire 51 is radio-opaque (FIGS. 2, 34, 36).

The surgeon removes the flexible sheath 19, the insertion system 20, and the guide elements of the bone channel Ca.

The surgeon attaches the end of the wires 50, 51 to the interior of the bone channel Ca by means of the attachment means or a seal 43 that also makes it possible to seal said bone channel. The wires 50, 51 thus make integral the nuclear implant 1 with the vertebra to preclude the potential migration problems.

The second wire 51 is designed to fill the remaining nuclear space Es, i.e., the central internal space 52 that is delimited by the first wire ring 50 that forms the pseudo-annulus. The second wire 51 is inserted under pressure using the gun 20 to ensure an adequate filling rate that is required for good compression strength.

The second wire 51 is arranged either according to a second ring or according to a ball, or according to both, forming a pseudo-nucleus. When the second ring or the ball of wire 51 forming the pseudo-nucleus is considered to be satisfactory, namely very dense, the second wire 51 is attached to the seal 43.

In the case where the filling element 2 is formed by, for example, a wire ring 50 that delimits a central internal space 52, the latter can be filled either by another wire 51 or by a product 53 that can be a gel or a pasty product or a fiber-based product. The filling element 2 is formed by, for example, a wire ring 50 and, partially filling the nuclear space Es, it makes it possible to create a pseudo-annulus, whose function will be to protect and reinforce the "annulus fibrosus" (AF)

and to prevent the risks of subsequent formation or degradation of the "annulus fibrosus" (AF).

Nuclear Implant 1 with Wire 50, 51 and a Product 53 that is of a Gel or Pasty Type or Fiber-Based or an Injectable Viscoelastic Material.

The filling element 2 can also be created from a single wire 50 in the shape of a ring whose central internal space 52 and the gaps 30 are filled by a product 53 that can be a gel or a pasty product or a fiber-based product or an injectable viscoelastic material that forms a "pseudo-nucleus" (FIG. 18).

The thus obtained nuclear implant 1 forms a neo-nucleus that has good mechanical characteristics of cohesion and shock absorption constituted by the wire ring 50 that forms a pseudo-annulus and a product 53 that can be a gel or a pasty product or a fiber-based product or an injectable viscoelastic material that forms a "pseudo-nucleus."

The filling element 2 can consist of a first wire ring 50 that delimits an internal central space 52 and a certain number of gaps 30 between the coils 55 of the winding, a second wire 51 that is arranged according to a second ring, and a product 53 that can be a gel or a pasty product or a fiber-based product or an injectable viscoelastic material that forms a "pseudo-nucleus" (FIG. 35).

The gaps 30 and the internal central space 52 of the nuclear implant 1 are filled with a product 53 that can be a gel or a pasty product or a fiber-based product or an injectable viscoelastic material.

When compression is exerted on the filling element 2, it has been observed that said filling element entrains forces of contact on wires 50, 51, locking them to one another. This locking provides to the filling element 2 a consistency that allows good mechanical behavior with compression forces and stability of the structure. The denser this structure is, the more rigid the behavior of the filling element 2.

This filling element 2 makes it possible to ensure good resistance to the required compression for a nuclear implant 1 while limiting the lateral forces. The limitation of the lateral forces in particular on the "annulus fibrosus" (AF) is a key point for such an implant so as to prevent the nervous compression phenomena that can take place by the external bulge of the "annulus fibrosus" (AF) of the intervertebral disk Di or by a discal hernia.

It is noted that the nuclear implant 1 according to this invention can be combined with a faceted prosthesis that is put in at the same time or in addition when said faceted prosthesis is already installed on the overlying and underlying vertebrae Va, Vb of the spine segment Sr.

The access pathways, described below, are provided by way of nonlimiting example making it possible for the surgeon to reach the "nucleus pulposus" (NP) of the intervertebral disk Di.

The pathway of percutaneous transpedicular access is created either by the overlying vertebra Va or by the underlying vertebra Vb of the spine segment Sr so as to reach the intervertebral disk Di by drilling the pedicle of said overlying vertebra Va or underlying vertebra Vb.

Furthermore, it should be understood that the preceding description has been given only by way of example and it in no way limits the scope of the invention if the same goal could be achieved by replacing the above-described embodiment details with any other equivalent items.

The invention claimed is:

1. A nuclear implant that forms, between the vertebral endplates of overlying and underlying vertebrae of a spine segment, an intervertebral support device, the implant comprising a single continuous wire capable of being arranged inside a nuclear space that is obtained after nucleotomy of an intervertebral disc, the single continuous wire capable of coiling inside the nuclear space and forming a stacked outer coil that is configured to span the nuclear space, the outer coil having a winding axis in a first direction that is normal to the vertebrae of the spine segment, an outer surface of the outer coil being configured to be concentrically located adjacent to an inner wall of the nuclear space; and the single continuous wire further capable of coiling inside the nuclear space and forming a plurality of stacked inner coils arranged inside the outer coil, a first inner coil having a winding axis in a second direction that is opposite to the first direction, an outer surface of the first inner coil being concentrically located adjacent to an inner surface of the outer coil, the outer surface of each additional inner coil of the plurality of inner coils being concentrically located adjacent to the inner surface of a preceding inner coil, and each additional inner coil having a winding axis in a direction that is opposite of the preceding inner coil, wherein the plurality of inner coils define a central space inside the implant, and the outer coil and the plurality of inner coils are configured to span the intervertebral disc between the two endplates.

2. The nuclear implant according to claim 1, wherein the single continuous wire comprises active ingredients that promote formation of fibroses inside the implant.

3. The nuclear implant according to claim 1, wherein the single continuous wire is created from bio-resorbable composite materials or braided materials.

4. The nuclear implant according to claim 1, wherein the single continuous wire comprises a free end that is narrowed or tapered to prevent injuries to tissue.

5. The nuclear implant according to claim 1, further comprising a seal configured to hold the single continuous wire on the vertebrae to prevent migration of said wire.

6. The device according to claim 1, wherein the single continuous wire has an outside diameter between 0.4 mm and 0.8 mm.

7. The nuclear implant according to claim 1, wherein the central internal space is filled with a product in the form of a gel, a paste, a fiber-based product or a viscoelastic material.

8. The nuclear implant according to claim 1, wherein the single continuous wire is radio-opaque.

* * * * *